US012799518B2

(12) United States Patent
Ishihara et al.

(10) Patent No.: US 12,799,518 B2
(45) Date of Patent: Nov. 17, 2026

(54) DETERMINATION METHOD, FLUORESCENCE MEASUREMENT DEVICE, AND TEST AGENT

(71) Applicants: Tokyo Dental College, Tokyo (JP); The Yoshida Dental Mfg. Co., Ltd., Tokyo (JP)

(72) Inventors: Kazuyuki Ishihara, Tokyo (JP); Wataru Kikuchi, Tokyo (JP); Mayumi Hosokawa, Tokyo (JP); Ai Ito, Tokyo (JP)

(73) Assignees: Tokyo Dental College, Tokyo (JP); The Yoshida Dental Mfg. Co., Ltd., Tokyo (JP)

( * ) Notice: Subject to any disclaimer, the term of this patent is extended or adjusted under 35 U.S.C. 154(b) by 675 days.

(21) Appl. No.: 17/633,028

(22) PCT Filed: Aug. 5, 2020

(86) PCT No.: PCT/JP2020/029939
§ 371 (c)(1),
(2) Date: Feb. 4, 2022

(87) PCT Pub. No.: WO2021/025043
PCT Pub. Date: Feb. 11, 2021

(65) Prior Publication Data

US 2022/0275421 A1 Sep. 1, 2022

(30) Foreign Application Priority Data

Aug. 7, 2019 (JP) ................................ 2019-145784

(51) Int. Cl.
*C12Q 1/04* (2006.01)
*B01L 3/00* (2006.01)
*G01N 21/77* (2006.01)

(52) U.S. Cl.
CPC .............. *C12Q 1/04* (2013.01); *B01L 3/5023* (2013.01); *B01L 2300/0654* (2013.01); *B01L 2300/069* (2013.01); *G01N 2021/7786* (2013.01)

(58) Field of Classification Search
CPC ......... G01N 33/56955; G01N 21/6428; G01N 33/581; G01N 33/582; G01N 21/6408;
(Continued)

(56) References Cited

U.S. PATENT DOCUMENTS

2009/0305296 A1 12/2009 Bengtsson et al.

FOREIGN PATENT DOCUMENTS

EP 0304871 A2 3/1989
JP H01107155 * 4/1989 ....... G01N 33/54366
(Continued)

OTHER PUBLICATIONS

Baek et al., (Virulence. Jan. 23, 2015;6(3):274-281). (Year: 2015).*
(Continued)

*Primary Examiner* — Jana A Hines
(74) *Attorney, Agent, or Firm* — GRUMBLES LAW PLLC; Bryan Kravis

(57) ABSTRACT

The present invention provides a determination method, a fluorescence measurement device, and a test agent, each of which can easily determine a genotype of a microorganism responsible for causing a periodontal disease, based on enzyme activity. The determination method of determining a genotype of the microorganism responsible for periodontal disease includes the steps of: irradiating a liquid sample with excitation light, the liquid sample including a bacterial body or a bacterial body-based extractive matter of the microorganism responsible for periodontal disease and a reagent in which a substrate for an enzyme reaction by the microorganism responsible for periodontal disease is fluorescently (Continued)

labeled, the liquid sample having a pH value thereof having been adjusted to not lower than pH 7.0 and not higher than pH 8.5 and then having been subjected to the enzyme reaction; and determining the genotype based on an intensity of fluorescence emitted from the liquid sample.

13 Claims, 21 Drawing Sheets

(58) Field of Classification Search
CPC ....... G01N 2800/18; G01N 2021/7786; G01N 2021/6439; C12M 1/34; C12Q 1/04; C12Q 1/37; C12Q 2600/156; B01L 2300/069; B01L 2300/0654; B01L 3/5023
See application file for complete search history.

(56) References Cited

FOREIGN PATENT DOCUMENTS

| | | | |
|---|---|---|---|
| JP | H01107155 | A | 4/1989 |
| JP | H01144997 | A | 6/1989 |
| JP | H05317095 | A | 12/1993 |
| JP | H06501692 | A | 2/1994 |
| JP | H11228597 | A | 8/1999 |
| JP | 2007519923 | A | 7/2007 |
| JP | 2010130924 | A | 6/2010 |
| WO | 1992006103 | A1 | 4/1992 |

OTHER PUBLICATIONS

Chen et al., (Caries Research. Jun. 2015 Caries Research 49(4):401-407). (Year: 2015).*

Amano, A., “Adhesive Capability and Genotypic Variation of Porphyromonas gingivalis Fimbriae in Relation to Periodontal Pathogenicity”, Osaka University Graduate School of Dentistry, 2003, 45(4), pp. 357-363.

International Search Report and Written Opinion pertaining to PCT/JP2020/029939, mailed Oct. 6, 2020.

Miura et al., “The proteinase activity and the level of coaggregation of Porphyromonas gingivalis with different fimA genotypes”, Section of Periodontology, Division of Oral Rehabilitation at Kyushu University, and Department of General Dentistry at Fukuoka Dental College, C-3-9:20.

* cited by examiner

FIG. 3A
pH7.0
pH7.5
pH7.8
pH7.9
pH8.0
pH8.5
Fluorescence intensity
1080
980
880
780
680
580
480
380
280
180
0
6
Measurement time [minute]

DETERMINATION METHOD, FLUORESCENCE MEASUREMENT DEVICE, AND TEST AGENT

CROSS REFERENCE TO RELATED APPLICATION

This application is a National Stage Application of PCT/JP2020/029939, filed on Aug. 5, 2020, and which application is incorporated herein by reference. To the extent appropriate, a claim of priority is made to the above disclosed application.

TECHNICAL FIELD

The present invention relates to a determination method, a fluorescence measurement device, and a test agent, each of which is used for determining a genotype of a microorganism responsible for causing a periodontal disease.

BACKGROUND ART

Several hundreds of different types of dental bacteria are present in a human mouth. Three of those dental bacteria, namely, *Porphyromonas gingivalis, Treponema denticola*, and *Tannerella forsythia*, are categorized as a red complex which is highly associated with a periodontal disease.

The periodontal disease is an inflammatory disorder caused by bacteria in the mouth and is considered to affect a periodontal tissue and also to be associated with a myocardial infarction, diabetes, and the like, as well as a systemic disease such as arteriosclerosis. Some of existing methods used for diagnosis of the periodontal disease include: a probing test in which a probe is used for determining a depth of a periodontal pocket or looking into whether or not gum is bleeding; and X-ray radiography for observing alveolar bone. Some test agents for in-vitro diagnosis of whether or not a microorganism responsible for periodontal disease is present, as described in Patent Documents 1 and 2.

In the fields of bacteriology and clinical medicine, it is considered that, of the three bacteria categorized as the red complex, *Porphyromonas gingivalis* (Pg) most significantly affects aggravation of the periodontal disease, that is, progression of destruction of alveolar bone. The Pg bacterium has fimbriae on a surface of its bacterial body. Some components on the surface of the bacterial body such as the fimbria are known to be heavily involved in adhesion and colonization into a mouth cavity.

One of genes that encodes a fimbrial protein of a Pg bacterium is a fimA gene that encodes a subunit of the fimbrial protein. The fimA gene is known to be polymorphic and is categorized into five types, types I to V (types 1 to 5). It has been reported that different genotypes of the fimA gene probably have different types of virulence, adhesion, and colonization ability into a mouth cavity of the Pg bacteria.

Non-Patent Document 1, for example, describes that about 70% of adults with healthy periodontal tissue have type I of the fimA gene; about 30%, type V; and about 10% or less, the others. Meanwhile, about slightly less than 60% of adults suffering from periodontitis have type II (type 2); about slightly less than 20%, type IV (type 4); and about slightly less than 10%, the others. More than 90% of the Pg bacteria detected from advanced periodontitis patients are reported to be type II.

RELATED ART DOCUMENTS

Patent Documents

Patent Document 1: Japanese Laid-Open Patent Application, Publication No. 2010-130924

Patent Document 2: Japanese Laid-Open Patent Application, Publication No. 2007-519923

Non-Patent Document

Non-Patent Document 1: Amano A. (2003), "Adhesive Capability and Genotypic Variation of *Porphyromonas gingivalis* Fimbriae in Relation to Periodontal Pathogenicity", Journal of Japanese Society of Periodontology, vol. 45(4), p 357-p 363.

SUMMARY OF THE INVENTION

Problems to be Solved by the Invention

It has been suggested that, as observed in the fimA gene of the Pg bacteria, different genotypes of the microorganism responsible for the periodontal disease have different influences on pathological conditions of the periodontal disease. Thus, in diagnosis, therapy, and prevention of the periodontal disease, if a genotype of a bacterial flora in the mouth of a patient is determined, there is a possibility that a pathological condition of the periodontal disease can be assessed more appropriately or a probability of aggravation thereof can be estimated.

Molecular biology techniques using RT-PCR or the like have been used as a method of determining a genotype. The molecular biology technique, however, requires a number of operations and is difficult to be performed easily. Additionally, though the molecular biology technique can count the number of copies of genes or cells indirectly, the technique cannot measure an enzyme activity which actually makes the periodontal disease advance.

Pg bacteria categorized as the red complex produces gingipain or the like, which is a type of protease. It is contemplated that an enzyme thereof causes disturbance of a bacterial flora such as dysbiosis or promotion of an inflammatory response, resulting in progression of the periodontal disease. Due to the described above, there is a need for a method of determining a genotype, which can be performed more easily, compared with conventional molecular biology techniques, is more in conformity with a pathological condition of the periodontal disease, and is based on a direct index.

In light of the described above, the present invention has been made in an attempt to provide a determination method, a fluorescence measurement device, and a test agent, each of which is used for easily determining a genotype of a microorganism responsible for causing a periodontal disease, based on enzyme activity.

Means for Solving the Problems

In order to solve the aforementioned problems, a determination method of determining a genotype of a microorganism responsible for periodontal disease of the present invention includes the steps of: irradiating a liquid sample with excitation light, the liquid sample including a bacterial body of the microorganism responsible for periodontal disease or a bacterial body-based extractive matter thereof and a reagent in which a substrate for an enzyme reaction by the microorganism responsible for periodontal disease is fluorescently labeled, the liquid sample having a pH value thereof having been adjusted to not lower than pH 7.0 and not higher than pH 8.5 and then having been subjected to the enzyme reaction; and determining the genotype based on an intensity of fluorescence emitted from the liquid sample.

A fluorescence measurement device determining a genotype of a microorganism responsible for periodontal disease of the present invention includes: an irradiator that irradiates a liquid sample with excitation light, the liquid sample including a bacterial body or a bacterial body-based extractive matter of the microorganism responsible for periodontal disease and a reagent in which a substrate for an enzyme reaction by the microorganism responsible for periodontal disease is fluorescently labeled, the liquid sample having a pH value thereof having been adjusted to not lower than pH 7.0 and not higher than pH 8.5 and then having been subjected to the enzyme reaction; a detector that detects fluorescence emitted from the liquid sample; and a determinator that determines a genotype of the target liquid sample, based on an intensity of the detected fluorescence.

A test agent that determines a genotype of a microorganism responsible for periodontal disease of the present invention includes: a reagent in which a substrate for enzyme reaction by the microorganism responsible for periodontal disease is fluorescently labeled; and a pH buffer solution which is a solution with the reagent dissolved therein. A pH of the pH buffer solution is not lower than pH 7.0 and not higher than pH 8.5.

Advantageous Effects of the Invention

The present invention can provide a determination method, a fluorescence measurement device, and a test agent, each of which can easily determine a genotype of a microorganism responsible for causing a periodontal disease, based on enzyme activity.

EMBODIMENT FOR CARRYING OUT THE INVENTION

<Determination Method/Test Agent>

Figure 1:
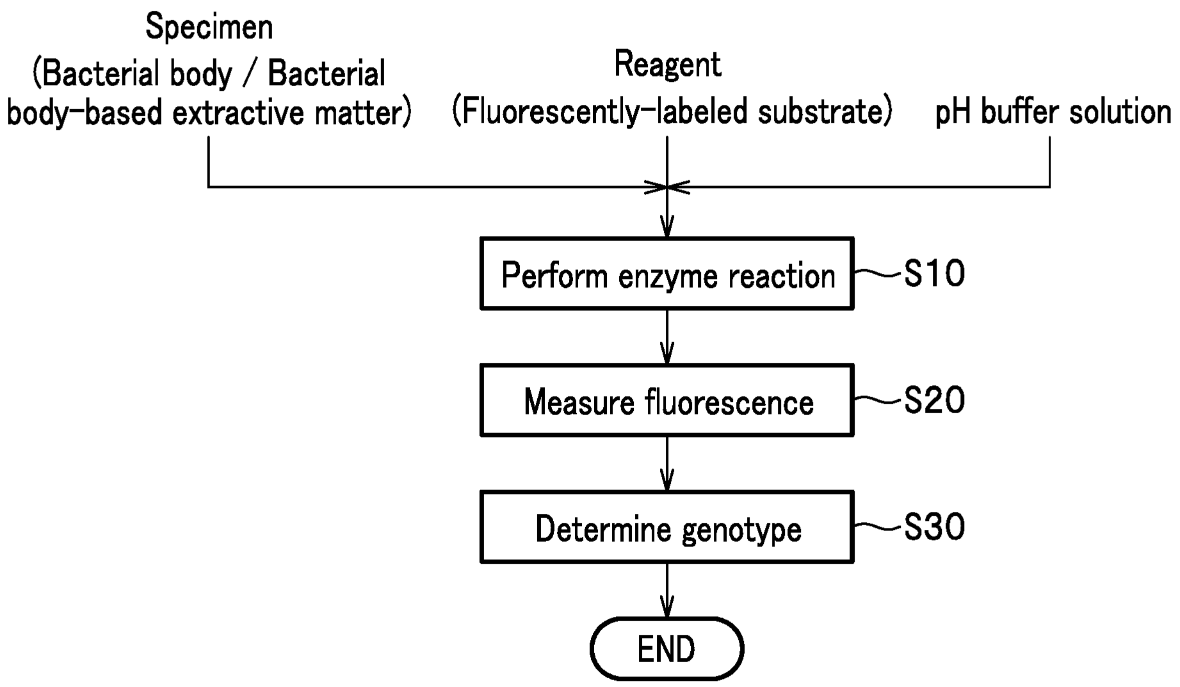
FIG. 1 is a flowchart illustrating steps of a determination method according to an embodiment of the present invention.

A determination method and a test agent each according to an embodiment of the present invention are described with reference to the related drawings.

The determination method according to the embodiment is a method of determining a genotype of an microorganism responsible for causing a periodontal disease. The determination method determines to which genotype a microorganism responsible for a periodontal disease collected in a sample belongs, from among known polymorphic types. Determination of the genotype is made based on enzyme activity regarding which correlation with each of the genotypes has been confirmed. The enzyme activity is assessed with a fluorometric method by using a test agent based on a fluorescently-labeled enzyme reaction substrate.

The microorganism responsible for periodontal disease whose genotype is to be determined herein includes *Porphyromonas gingivalis* (Pg). The genotype to be determined includes type I (type 1), type II (type 2), type III (type 3), type IV (type 4), and type V (type 5), each of which is a polymorphic type of the fimA gene that encodes fimbrial protein. It is assumed herein that type Ib which is a subtype of the fimA gene belongs to type I.

In the determination method according to the embodiment, a bacterial body or a bacterial body-based extractive matter of a microorganism responsible for periodontal disease or, whose genotype is not yet known (a specimen), is added to a liquid test agent containing a fluorescently-labeled enzyme reaction substrate (a fluorescently-labeled substrate), to thereby prepare a liquid sample for fluorescence measurement. The fluorescently-labeled substrate is a substrate of a degrading enzyme produced by an microorganism responsible for periodontal disease and dissociates a fluorescent chromophore by enzyme reaction. The dissociated fluorescent chromophore yields a fluorescence in response to irradiation with excitation light. Intensity of the fluorescence emitted from the liquid sample can be thus used as an index of the enzyme activity.

If there is a correlation between an enzyme activity and a genotype of a specimen, the specimen can be categorized into any one of the genotypes, based on the enzyme activity determined by the fluorescence measurement. If an enzyme reaction is performed under a condition under which differences in enzyme activity depending on different genotypes are made clear, differences in fluorescent intensity emitted from the liquid sample becomes larger, thus allowing a genotype of the specimen to be distinctively determined.

A specimen used herein in preparing a liquid sample for fluorescence measurement so as to determine a genotype is a bacterial body or a bacterial body-based extractive matter of an microorganism responsible for periodontal disease, whose genotype is not yet known. Some examples of the specimen include dental plaque, and gingival fluid taken from the mouth of a subject, as it is or in form of suspension liquid or supernatant thereof. Microorganisms responsible for periodontal disease in bacterial flora in the mouth of a human or the like are typically present in a state in which any one of the genotypes is dominant. This allows a bacteria specimen collected from a subject to be categorized into any one of the genotypes which is dominant over the others.

A liquid sample for fluorescence measurement may be prepared by adding a bacterial body contained in dental plaque, gingival fluid, or the like, to a liquid test agent containing a fluorescently-labeled substrate or may be prepared by adding a bacterial body-based extractive matter extracted from a bacterial body thereto. Note that as far as the bacterial body-based extractive matter contains a degrading enzyme that reacts with the fluorescently-labeled substrate, the bacterial body-based extractive matter includes both an extractive matter obtained by performing a cell destruction treatment or the like to a bacterial body and separating the residue, and a secretion exogenously secreted or produced by the bacterial body.

FIG. 1 is a flowchart illustrating steps of a determination method according to an embodiment of the present invention.

As illustrated in FIG. 1, the determination method according to the embodiment includes an enzyme reaction step S10, a fluorescence measurement step S20, and a genotype determination step S30.

In the enzyme reaction step S10, a bacterial body or a bacterial body-based extractive matter of a microorganism responsible for periodontal disease, whose genotype is not yet known (a specimen) is added to a liquid test agent containing a fluorescently-labeled substrate (a test agent) and a pH buffer solution, to thereby start an enzyme reaction. The fluorescently-labeled substrate is a substance whose substrate for enzyme reaction by the microorganism responsible for periodontal disease is fluorescently labeled by fluorescent chromophore. The liquid test agent in which the enzyme reaction has started by adding the specimen corresponds to a liquid sample to be measured using a fluorometric method.

A substance preferably but not necessarily used as the fluorescently-labeled substrate is that having a L-arginine (Arg) residue with a polypeptide at the C-terminal and having the Arg residue at the C-terminal bound to the fluorescent chromophore. Usage of the fluorescently-labeled substrate as described above makes it possible to assess enzyme activity of a Pg bacterium because gingipain which is a protease produced thereby specifically digests the C-terminal of the Arg residue.

The fluorescently-labeled substrate may have any amino acid sequence, as far as the amino acid sequence is recognized by a protease produced by the microorganism responsible for periodontal disease. A polypeptide constituting the fluorescently-labeled substrate may be composed of any number or any types of amino acids. The polypeptide is, however, preferably but not necessarily 3- to 4-mer in length from a viewpoint of a stable enzyme reaction or a stable fluorescence measurement.

The fluorescently-labeled substrate may have the N-terminal of the polypeptide protected by a protective group. Some examples of the protective group include an isobutyl oxycarbonyl group (iBOC), a tert-butoxycarbonyl group (Boc), an acetyl group (Ac), a benzoyl group (Bz), and a 9-fluorenylmethoxycarbonyl group (Fmoc).

The fluorescently-labeled substrate is preferably but not necessarily bound to aminomethylcoumarin (AMC) as the fluorescent chromophore. Usage of the AMC makes it possible to yield no fluorescence in a state of amide binding and to produce fluorescence only in a state of dissociation, to thereby obtain a high intensity fluorescence. The enzyme activity can be thus assessed by a highly sensitive fluorescence measurement.

An example preferably but not necessarily used as the fluorescently-labeled substrate is in particular a protective-group-glycyl-glycyl-L-arginyl-4-methylcoumaryl-7-amide (Gly-Gly-Arg-MCA). Usage of the fluorescently-labeled substrate as above makes it possible to be recognized by gingipain produced by Pg bacteria more easily, which allows a high intensity suitable for measurement by the AMC. Enzyme activity of the Pg bacteria can be thus assessed more accurately.

A liquid sample subjected to fluorescence measurement may be preferably but not necessarily a pH buffer solution containing, as a major component thereof, either trihydroxymethylaminomethane (Tris), piperazine-1,4-bis(2-ethanesulfonate) (PIPES), or 2-[4-(2-hydroxyethyl) piperazinyl] ethanesulfonate (HEPES). Usage of the pH buffer solution as described above makes it possible to keep the pH at a level suitable for gingipain produced by the Pg bacteria, thus allowing the enzyme activity of the Pg bacteria to be assessed accurately.

The liquid sample subjected to the fluorescence measurement is preferably but not necessarily is in particular a pH buffer solution containing trihydroxymethylaminomethane (Tris) as a major component thereof. Some of specific examples of the Tris-based pH buffer solution include a Tris-hydrochloride buffer solution, a Tris-acetate buffer solution, a Tris-borate buffer solution, and a Tris-phosphate buffer solution. The Tris-based pH buffer solution makes it possible to assess enzyme activity of the Pg bacteria more accurately.

In the fluorescence measurement step S20, the liquid sample is irradiated with excitation light and an intensity of fluorescence emitted from liquid sample is measured. The liquid sample is a solution containing: a bacterial body or a bacterial body-based extractive matter of a microorganism responsible for periodontal disease, whose genotype is not yet known (a specimen); and a fluorescently-labeled substrate in which a substrate for enzyme reaction by the microorganism responsible for periodontal disease is fluorescently labeled (a reagent). The fluorescently-labeled substrate dissociates a fluorescent chromophore by enzyme reaction caused by a degrading enzyme produced by the microorganism responsible for periodontal disease and thus emits fluorescence in response to the irradiation with the excitation light at a prescribed wavelength. Thus, in performing a fluorescence measurement, a fluorescence intensity in accordance with an enzyme activity and a reaction time of a bacteria specimen can be detected.

A wavelength at which the liquid sample is irradiated with the excitation light is: preferably but not necessarily, not less than 350 nm and not more than 380 nm; more preferably but not necessarily, not less than 355 nm and not more than 375 nm; and, still more preferably but not necessarily, not less than 360 nm and not more than 370 nm. Usage of the wavelength as described above makes it possible to obtain a fluorescence intensity suitable for detection, when a fluorescent chromophore constituting the fluorescently-labeled substrate is AMC.

A wavelength at which the fluorescence intensity is measured is: preferably but not necessarily, not less than 410 nm and not more than 475 nm; more preferably but not necessarily, not less than 425 nm and not more than 465 nm; and, still more preferably but not necessarily, not less than 435 nm and not more than 450 nm. Usage of the wavelength as described above makes it possible to detect fluorescence with a high sensitivity, when a fluorescent chromophore constituting the fluorescently-labeled substrate is AMC.

Note that the detection of fluorescence from the liquid sample is preferably but not necessarily made after the specimen is added to the liquid test agent containing the fluorescently-labeled substrate, and, before the fluorescently-labeled substrate is completely discomposed and dissociated by the enzyme reaction. Additionally, the detection of fluorescence from the liquid sample is preferably but not necessarily made, before the fluorescence decays in the course of a fluorescence lifetime.

In the genotype determination step S30, a genotype of the microorganism responsible for periodontal disease, whose genotype is not yet known (the bacteria specimen) is detected, based on the fluorescence intensity emitted from the liquid sample in response to the irradiation with the excitation light. A value of the fluorescence intensity detected by the fluorescence measurement indirectly indicates a reaction rate of the enzyme reaction, that is, a rate of the reacted substrate. An amount of change of the fluorescence intensity over time indirectly indicates a reaction rate of the enzyme. This makes it possible to determine a genotype of the microorganism responsible for periodontal disease, based on those index values of the fluorescence intensity, if there is a correlation between the enzyme activity and the genotype of the responsible microorganism.

Next are described how to specifically determine a genotype of a microorganism responsible for periodontal disease and a method thereof, with reference to related drawings.

Figure 2A:
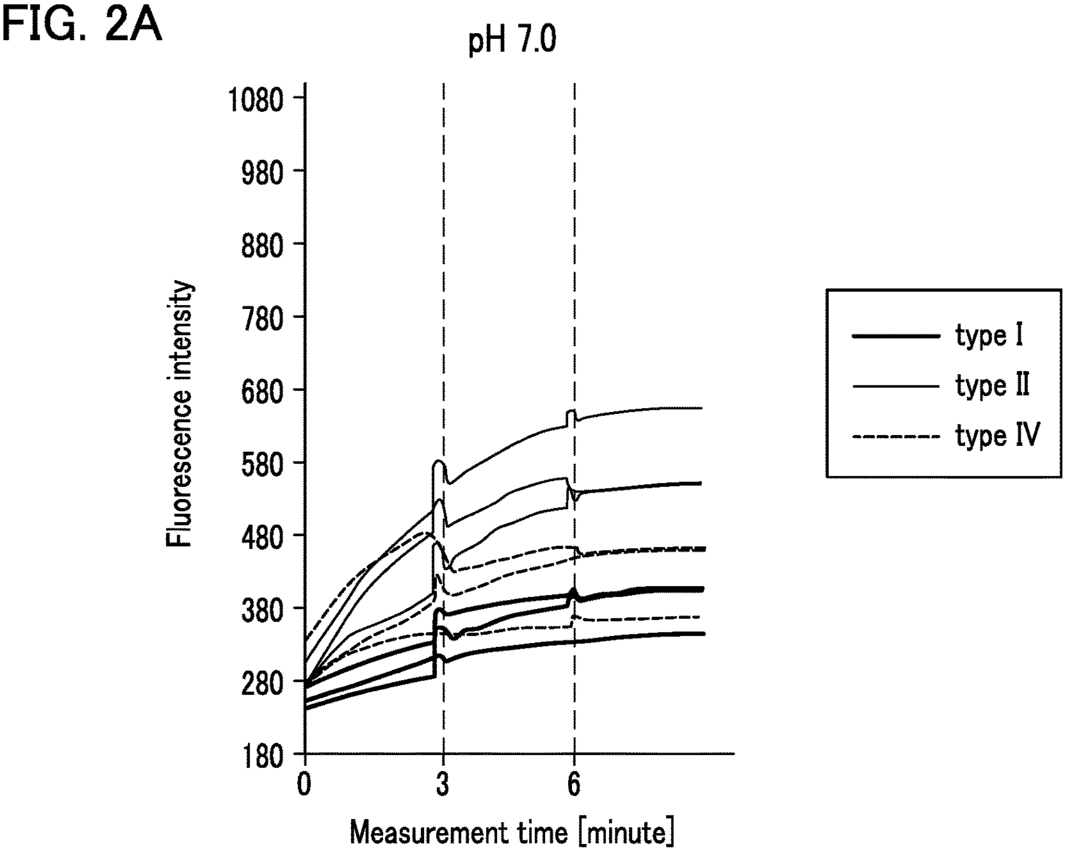
FIG. 2A is a diagram illustrating a result of a fluorescence measurement of a liquid sample (pH 7.0) in which a bacterial body has been subjected to enzyme activity.
Figure 2B:
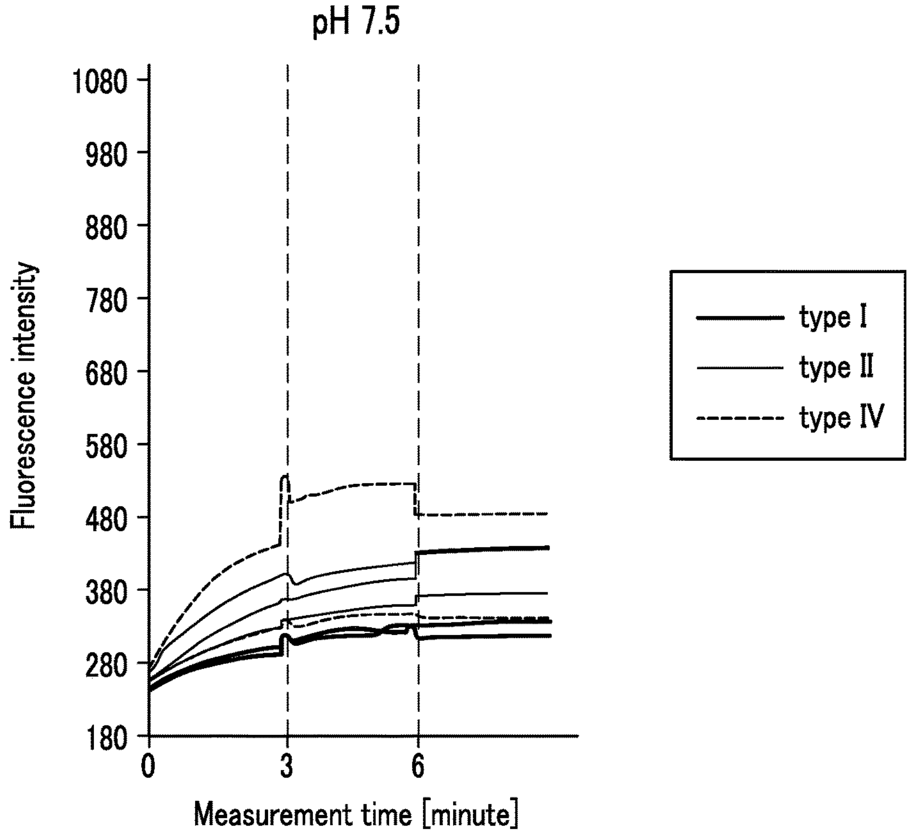
FIG. 2B is a diagram illustrating a result of a fluorescence measurement of a liquid sample (pH 7.5) in which a bacterial body has been subjected to enzyme activity.
Figure 2C:
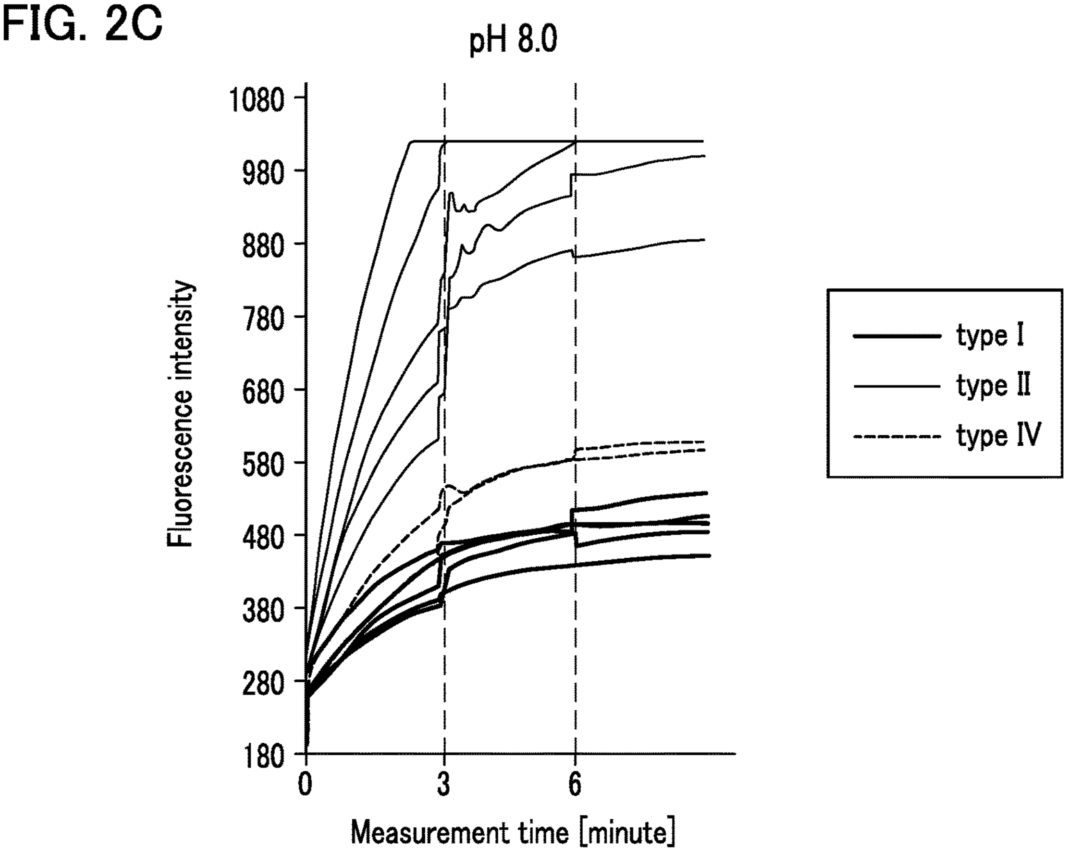
FIG. 2C is a diagram illustrating a result of a fluorescence measurement of a liquid sample (pH 8.0) in which a bacterial body has been subjected to has been subjected to enzyme activity.
Figure 2D:
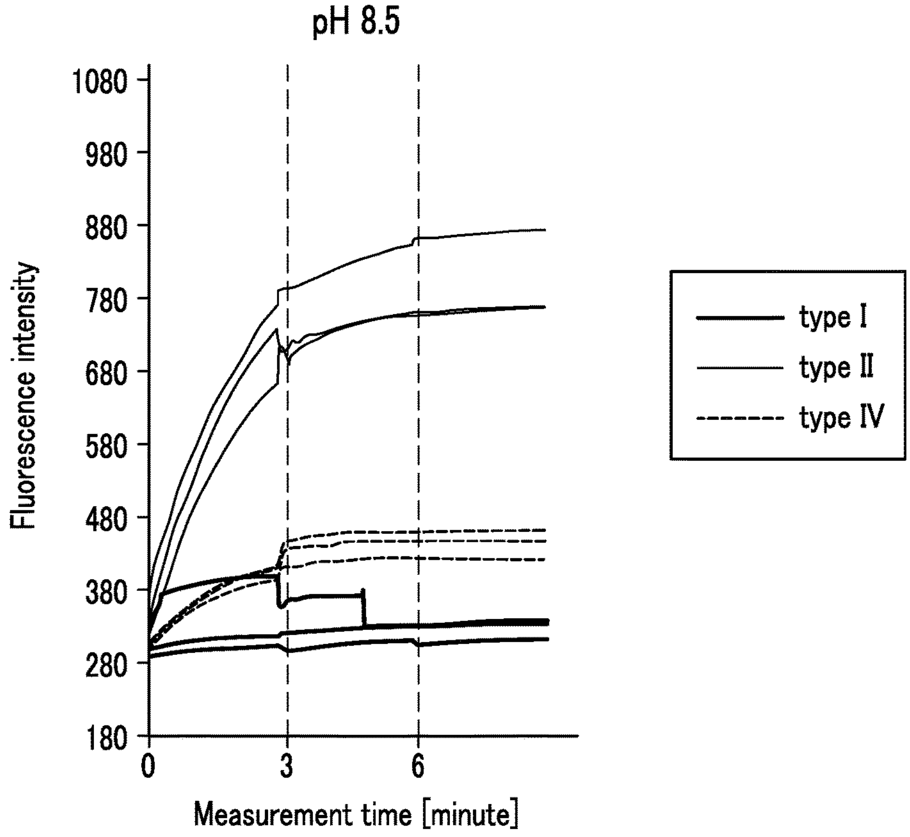
FIG. 2D is a diagram illustrating a result of a fluorescence measurement of a liquid sample (pH 8.5) in which a bacterial body has been subjected to enzyme activity.
Figure 2E:
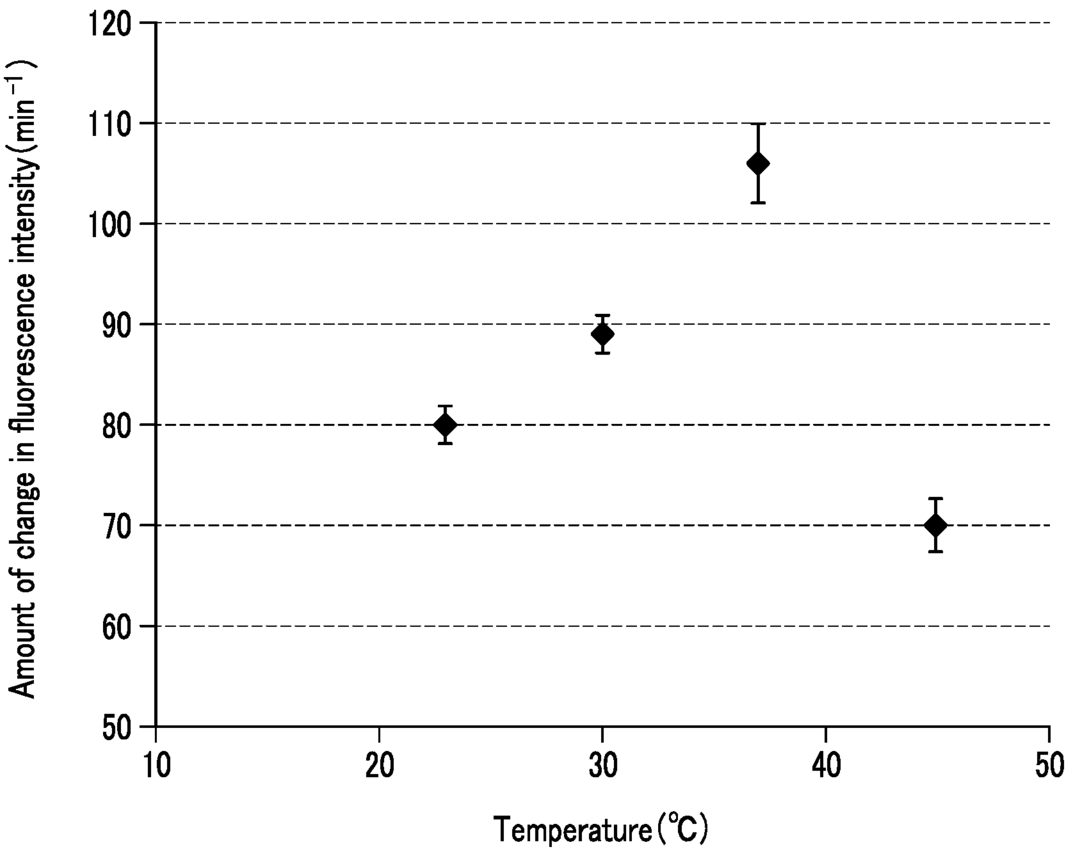
FIG. 2E is a diagram illustrating a result of a fluorescence measurement of a liquid sample in which an enzyme having a property similar to that of gingipain has been subjected to enzyme reaction at different temperatures.

FIGS. 2A to 2E are each a diagram illustrating a result of a fluorescence measurement of a liquid sample in which a bacterial body has been subjected to enzyme reaction. FIG. 2A illustrates a result under a condition of the enzyme reaction at pH 7.0; FIG. 2B, at pH 7.5; FIG. 2C, at pH 8.0; and FIG. 2D, at pH 8.5. FIG. 2E illustrates a result of a fluorescence measurement of a liquid sample in which an enzyme having a property similar to that of gingipain has been subjected to enzyme reaction at different temperatures.

FIG. 2A to FIG. 2D each illustrates the result obtained by: separating a cell suspension liquid of Pg bacteria by centrifugalization; collecting a deposit therefrom; preparing a liquid sample to which the deposit containing a bacterial body of the Pg bacteria is added; adjusting a pH of the liquid sample to an appropriate pH condition; subjecting the liquid sample to enzyme reaction at a temperature of 37.5° C.; and measuring a fluorescence intensity of the liquid sample using a fluorescence measurement device. FIG. 2E illustrates the result obtained by measuring a fluorescence intensity of another liquid sample to which trypsin having a property similar to that of gingipain, while changing a temperature of another liquid sample in a range from 23° C. to 45° C.

In each of FIG. 2A to FIG. 2D, the abscissa represents a measurement time [minute] starting at a beginning of the enzyme reaction, and the ordinate represents a fluorescence intensity in a prescribed unit. Each of the bold lines in the figures represents a result of Pg bacteria whose genotype of a fimA gene is type I. Each of the thin lines therein represents a result of Pg bacteria whose genotype of a fimA gene is type II. Each of the dashed lines therein represents a result of Pg bacteria whose genotype of a fimA gene is type IV. Each of the supplementary lines therein represents timing of relaying (switching) the fluorescence measurement device.

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for each of the genotypes is three.

As illustrated in FIG. 2A to FIG. 2D, the resultant fluorescence intensities vary depending on the different genotypes of the fimA gene. It is demonstrated that type IV generally has a value of fluorescence intensity at each of the measurement times higher than that of type I; and, type II, higher than that of type IV. In particular, when a pH value is controlled at pH 8.0 or pH 8.5, differences between the respective fluorescence intensity values for each of the genotypes become larger. It is found that the enzyme activity varies depending on different genotypes of the microorganism responsible for periodontal disease and is dependent on the pH.

It is demonstrated from the results shown in FIG. 2A to FIG. 2D that in a technique of adding a bacterial body to a liquid sample containing a fluorescently-labeled substrate, when the obtained liquid sample with the pH value controlled at higher than pH 7.5 and not higher than pH 8.5 is subjected to the enzyme reaction, the fluorescence intensities of type II and type IV become strong, which allows accuracy in determining a genotype of interest to be improved.

In FIG. 2E, the abscissa represents a temperature [° C.] of the liquid sample to which trypsin is added. The ordinate represents an amount of change over time in the fluorescence intensity per one minute. The amount of change over time in the fluorescence intensity is obtained by: measuring a fluorescence 10 minutes after starting the enzyme reaction; and converting the measured result into an amount of change per one minute. Plots in the figure represent respective average values of the amounts of change at the temperatures of 23° C., 30° C., 37° C., and 45° C. of the liquid samples. Respective error bars represent the maximum and the minimum values of each of the average values.

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for the each temperature is three.

As illustrated in FIG. 2E, it can be found that trypsin having the property similar to gingipain is temperature-dependent. The amounts of change over time in the fluorescence intensity increase in a temperature range from 23° C. to 37° C., and, by contrast, sharply decrease in a temperature range from about 37° C. to 45° C. The result obtained by the use of trypsin shows that the enzyme that degrades the fluorescently-labeled substrate has an optimum temperature thereof at about 37° C.

It is demonstrated from the result shown in FIG. 2E that, when trypsin having the property similar to that of gingipain is subjected to the enzyme reaction in the liquid sample whose temperature is controlled at not less than about 25° C. and not more than about 40° C., especially, at about 37° C.±1° C., a change in the fluorescence intensity caused by the enzyme reaction becomes large. This can contribute to an improved accuracy in determining a genotype.

Figure 3A:
FIG. 3A is a diagram illustrating a result of fluorescence measurement of a liquid sample for each pH, in which a bacterial body has been subjected to enzyme reaction.

FIG. 3A is a diagram illustrating a result of fluorescence measurement of a liquid sample for each pH, in which a bacterial body has been subjected to enzyme reaction.

FIG. 3A illustrates a result obtained by: separating a cell suspension liquid of Pg bacteria whose genotype of the fimA gene is type II, by centrifugalization; collecting a deposit therefrom; preparing a liquid sample to which the deposit containing a bacterial body of the Pg bacteria is added; adjusting a pH of the liquid sample to an appropriate pH condition; subjecting the liquid sample to enzyme reaction at a temperature of 37.5° C.; and measuring a fluorescence intensity of the liquid sample using a fluorescence measurement device.

In FIG. 3A, the abscissa represents a measurement time [minute] starting at a beginning of the enzyme reaction, and the ordinate represents a fluorescence intensity in a prescribed unit. Each of the thick dashed lines in the figure represents a result under a pH condition at pH 7.0; each of the dash-dot-dash lines, at pH 7.5; each of the slightly-thick dashed lines, at pH 7.8; each of the thin dashed lines, at pH 7.9; each of the thick solid lines, at pH 8.0; and, each of the thin solid lines, at pH 8.5.

The fluorescently-labeled substrate used herein is isobutyloxycarbonyl-glycyl-glycyl-L-arginyl-4-methylcoumaryl-7-amide (iBoc-Gly-Gly-Arg-MCA), The number of liquid samples for the each pH is three.

As illustrated in FIG. 3A, the resultant fluorescence intensities vary depending on the pH of the liquid sample. It is demonstrated that the liquid samples at pH 7.8 to pH 8.5 each have a value of fluorescence intensity at each of the measurement times and an amount of change over time in the fluorescence intensity in an early stage thereof higher than those at pH 7.0. The liquid samples at pH 7.9 and pH 8.0 each have in particular a large value of the fluorescence intensity, showing that there is a local maximal value at or near pH 8.0.

It is demonstrated from the results illustrated in FIG. 3A that in a technique of adding a bacterial body to a liquid sample containing a fluorescently-labeled substrate, when the obtained liquid sample with the pH value controlled at not lower than pH 7.8 and not higher than pH 8.5, especially, not lower than pH 7.8 and not higher than pH 8.5, is subjected to enzyme reaction, the fluorescence intensity becomes strong, which allows an improved accuracy in determining a genotype of interest.

Figure 3B:
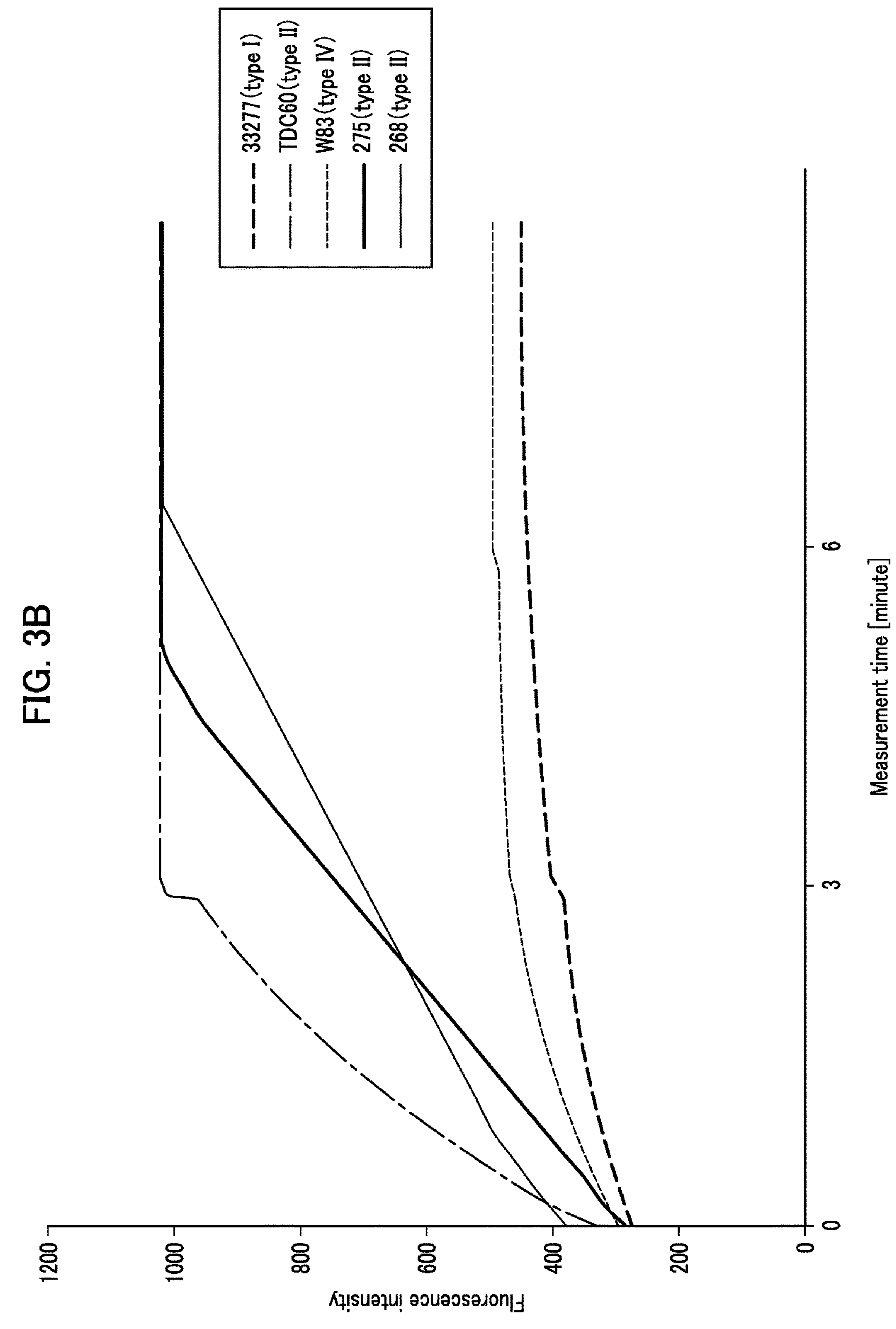
FIG. 3B is a diagram illustrating a result of fluorescence measurement of a liquid sample for each strain, in which a bacterial body has been subjected to enzyme reaction.

FIG. 3B is a diagram illustrating a result of fluorescence measurement of a liquid sample for each strain, in which a bacterial body has been subjected to enzyme reaction.

FIG. 3B illustrates a result obtained by: separating a cell suspension liquid of each of Pg bacteria whose types of strain are different from each other, by centrifugalization; collecting a deposit therefrom; preparing a liquid sample to which the deposit containing a bacterial body of the Pg bacteria is added; adjusting a pH of the liquid sample to an appropriate pH condition; subjecting the liquid sample to enzyme reaction at a temperature of 37.5° C.; and measuring a fluorescence intensity of the liquid sample using a fluorescence measurement device.

In FIG. 3B, the abscissa represents a measurement time [minute] starting at a beginning of the enzyme reaction, and the ordinate represents a fluorescence intensity in a prescribed unit. The long dashed line in the figure represents a result of a strain 33277 whose genotype of the fimA gene is type I; the dash-dot-dash line, a strain TDC 60, type II; the short dashed line, a strain W83, type IV; the thick solid line, a strain 275, type II; and the thin solid line, a strain 268, type II. Each of the strain 275 and the strain 268 is a strain isolated from subgingival dental plaque (see Hiroyuki Asano et al., Journal of Periodontology, 2003, Vol. 74, 9, p. 1355-1360).

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for the each strain is one.

As illustrated in FIG. 3B, the resultant fluorescence intensities vary depending on the genotypes of the fimA gene. It is, however, demonstrated that the strains TDC 60, 275, and 268 whose genotypes of the fimA gene are type II, each have a value of fluorescence intensity at each of the measurement times and an amount of change over time in the fluorescence intensity similar to each other, in spite of their different types of strains.

The result illustrated in FIG. 3B shows that, though enzyme activity of a degrading enzyme produced by the Pg bacteria varies for each of the genotypes of the microorganism responsible for periodontal disease, enzyme activity of the strains having the same genotype are similar to each other. This means that any appropriate strain can be used in determining a genotype based on a result of a fluorescence intensity thereof.

Figure 4A:
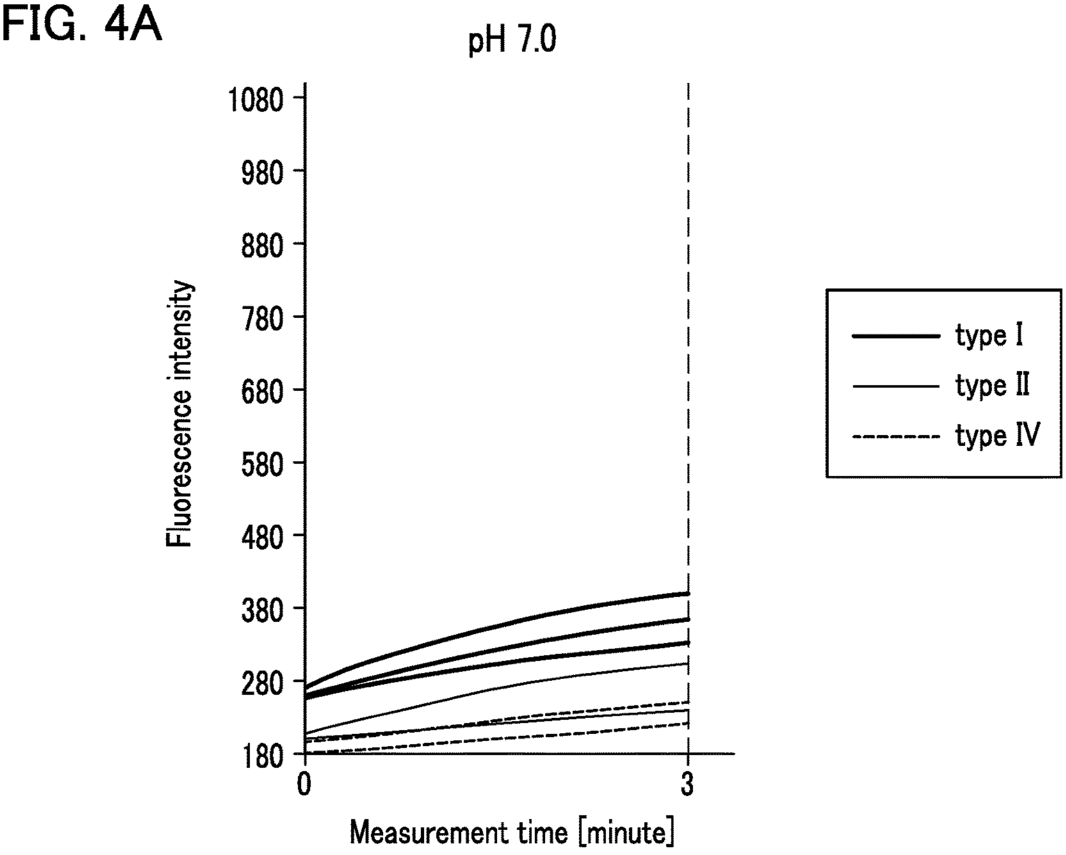
FIG. 4A is a diagram illustrating a result of fluorescence measurement of a liquid sample (pH 7.0) in which a bacterial body-based extractive matter has been subjected to enzyme reaction.
Figure 4B:
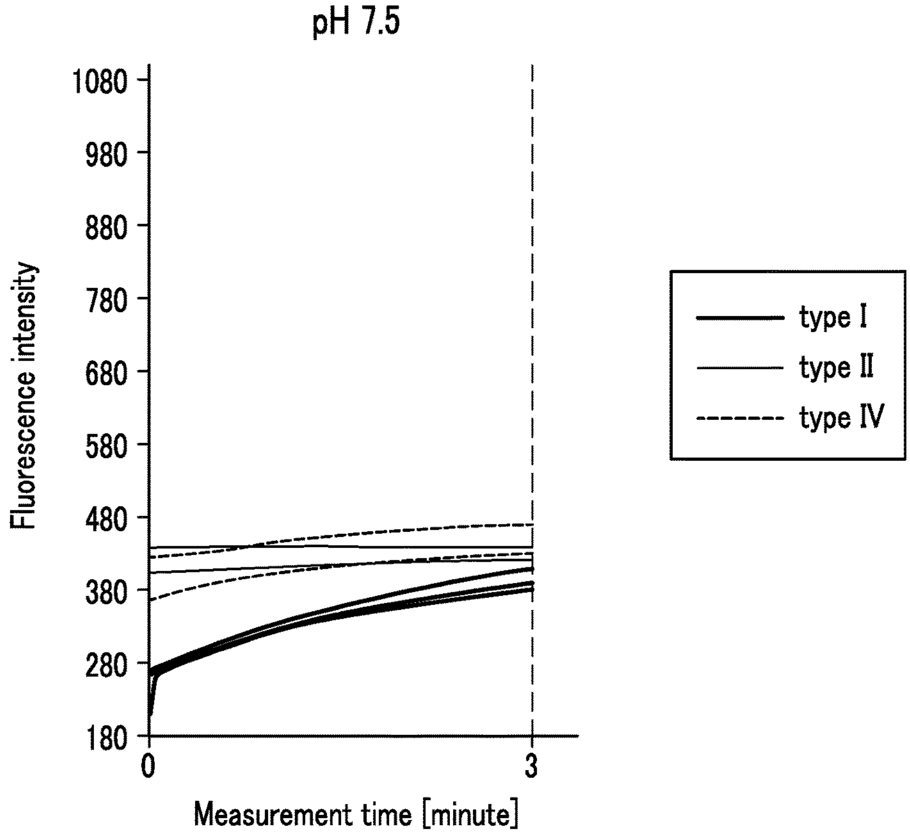
FIG. 4B is a diagram illustrating a result of fluorescence measurement of a liquid sample (pH 7.5) in which a bacterial body-based extractive matter has been subjected to enzyme reaction.
Figure 4C:
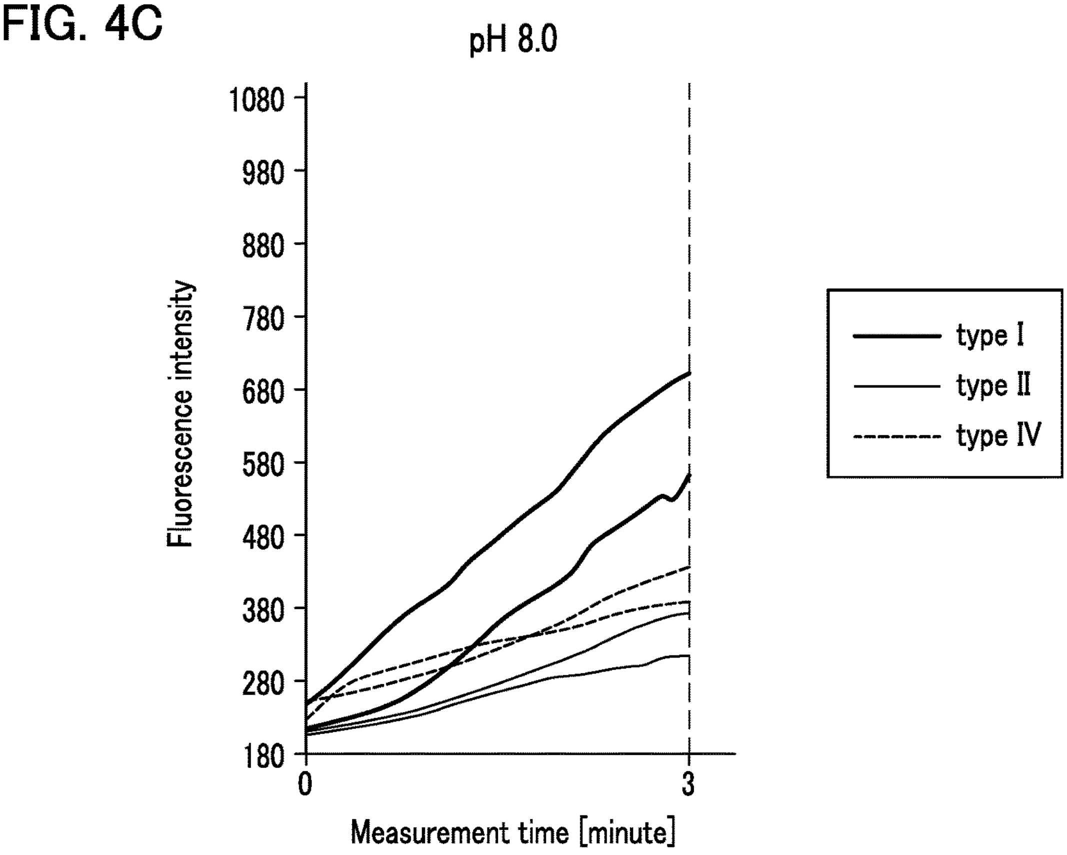
FIG. 4C is a diagram illustrating a result of fluorescence measurement of a liquid sample (pH 8.0) in which a bacterial body-based extractive matter has been subjected to enzyme reaction.
Figure 4D:
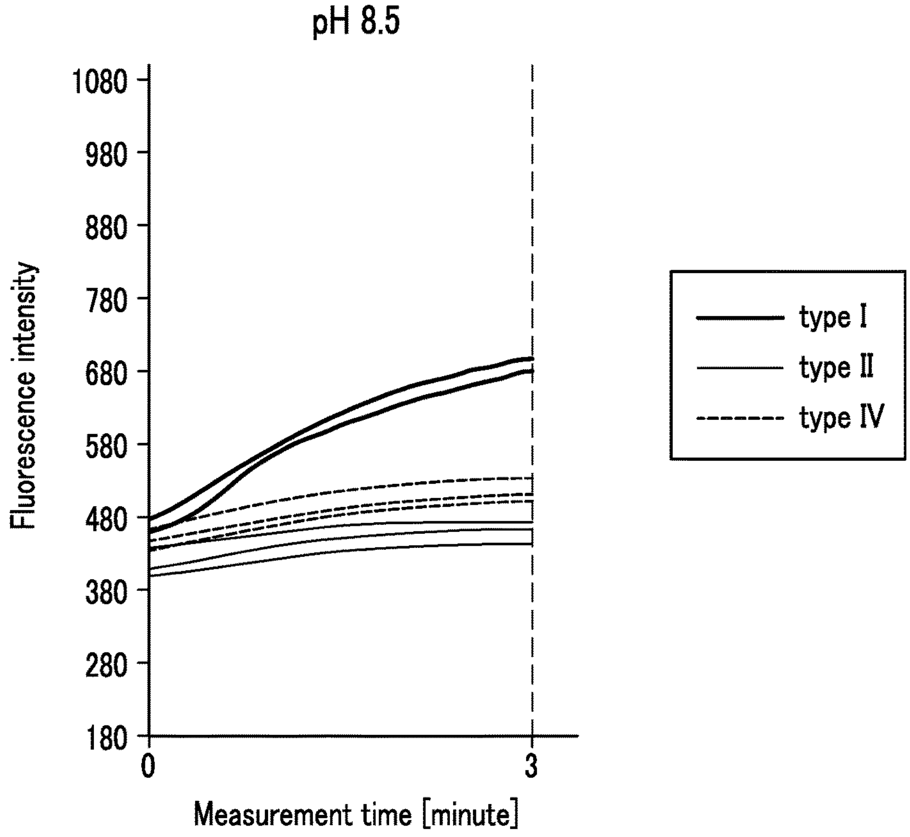
FIG. 4D is a diagram illustrating a result of fluorescence measurement of a liquid sample (pH 8.5) in which a bacterial body-based extractive matter has been subjected to enzyme reaction.

FIGS. 4A to 4D are each a diagram illustrating a result of a fluorescence measurement of a liquid sample in which a bacterial body-based extractive matter has been subjected to enzyme reaction. FIG. 4A illustrates a result under a condition of the enzyme reaction at pH 7.0; FIG. 4B, at pH 7.5; FIG. 4C, at pH 8.0; and FIG. 4D, at pH 8.5.

FIG. 4A to FIG. 4D each illustrate the result obtained by: separating a cell suspension liquid of Pg bacteria by centrifugalization; collecting supernatant therefrom; preparing a liquid sample to which the supernatant as a bacterial body-based extractive matter is added; adjusting a pH of the liquid sample to an appropriate pH condition; subjecting the liquid sample to enzyme reaction at a temperature of 37.5° C.; and measuring a fluorescence intensity of the liquid sample using a fluorescence measurement device.

In each of FIG. 4A to FIG. 4D, the abscissa represents a measurement time [minute] starting at a beginning of the enzyme reaction, and the ordinate represents a fluorescence intensity in a prescribed unit. Each of the bold lines in the figures represents a result of Pg bacteria whose genotype of the fimA gene is type I; each of the thin lines, type II; and, each of the dashed lines, type IV.

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for each of the genotypes is three.

As illustrated in FIG. 4A to FIG. 4D, the resultant fluorescence intensities vary depending on the different genotypes of the fimA gene. It is demonstrated that type IV generally has a value of fluorescence intensity at each of the measurement times higher than that of type IV; and, type I, higher than that of type IV. In particular, when a pH value is controlled at pH 8.0 or pH 8.5, differences between the fluorescence intensity values for each of the genotypes become larger. It is thus found that the enzyme activity varies depending on different genotypes of the microorganism responsible for periodontal disease and is dependent on the pH.

It is demonstrated from the results shown in FIG. 4A to FIG. 4D that in a technique of adding a bacterial body-based extractive matter to a liquid sample containing a fluorescently-labeled substrate, when the obtained liquid sample with the pH value controlled at higher than pH 7.5 and not higher than pH 8.5 is subjected to enzyme reaction, the fluorescence intensity of type I becomes strong, which allows an improved accuracy in determining a genotype. Additionally, when the obtained liquid sample with the pH value controlled at about pH 8.0 is subjected to enzyme reaction, the fluorescence intensities of type I and type IV become strong, which allows an improved accuracy in determining a genotype.

Figure 5:
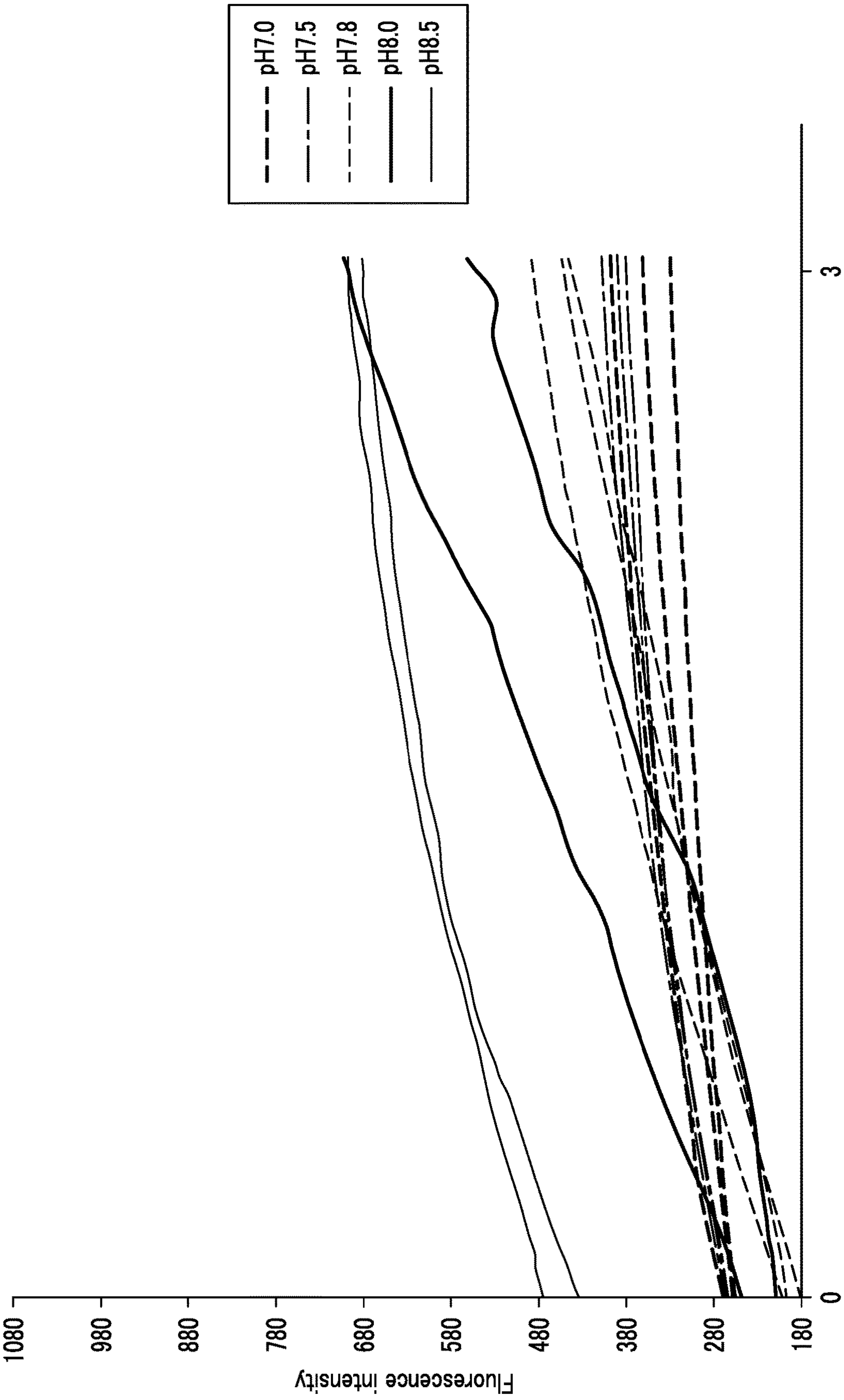
FIG. 5 is a diagram illustrating a result of fluorescence measurement of a liquid sample for each pH, in which a bacterial body-based extractive matter has been subjected to enzyme reaction.

FIG. 5 is a diagram illustrating a result of a fluorescence measurement of a liquid sample for each pH, in which a bacterial body-based extractive matter has been subjected to enzyme reaction.

FIG. 5 illustrates the result obtained by: separating a cell suspension liquid of Pg bacteria whose genotype of the fimA gene is type I, by centrifugalization; collecting supernatant therefrom; preparing a liquid sample to which the supernatant as a bacterial body-based extractive matter is added; adjusting a pH of the liquid sample to an appropriate pH condition; subjecting the liquid sample to enzyme reaction at a temperature of 37.5° C.; and measuring a fluorescence intensity of the liquid sample using a fluorescence measurement device.

In FIG. 5, the abscissa represents a measurement time [minute] starting at a beginning of the enzyme reaction, and the ordinate represents a fluorescence intensity in a prescribed unit. Each of the thick dashed lines in the figure represents a result of the Pg bacteria at pH 7.0; each of the dash-dot-dash lines, at pH 7.5; each of the thick solid lines, at pH 8.0; and, each of the thin solid lines, at pH 8.5.

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for the each pH is three.

As illustrated in FIG. 5, the resultant fluorescence intensities vary depending on the pH of the liquid sample. It is demonstrated that the liquid samples at pH 8.0 to pH 8.5 mostly have a value of fluorescence intensity at each of the measurement times and an amount of change over time in the fluorescence intensity higher than those at pH 7.0. The liquid samples at pH 8.0 each have in particular a large value of the fluorescence intensity, showing that there is a local maximal value near or not lower than pH 8.0.

It is demonstrated from the results shown in FIG. 5 that in a technique of adding a bacterial body-based extractive matter to a liquid sample containing a fluorescently-labeled substrate, when the obtained liquid sample with the pH value controlled at not lower than pH 8.0 and not higher than pH 8.5 is subjected to enzyme reaction, the fluorescence intensity becomes stronger, which allows an improved accuracy in determining a genotype.

Figure 6A:
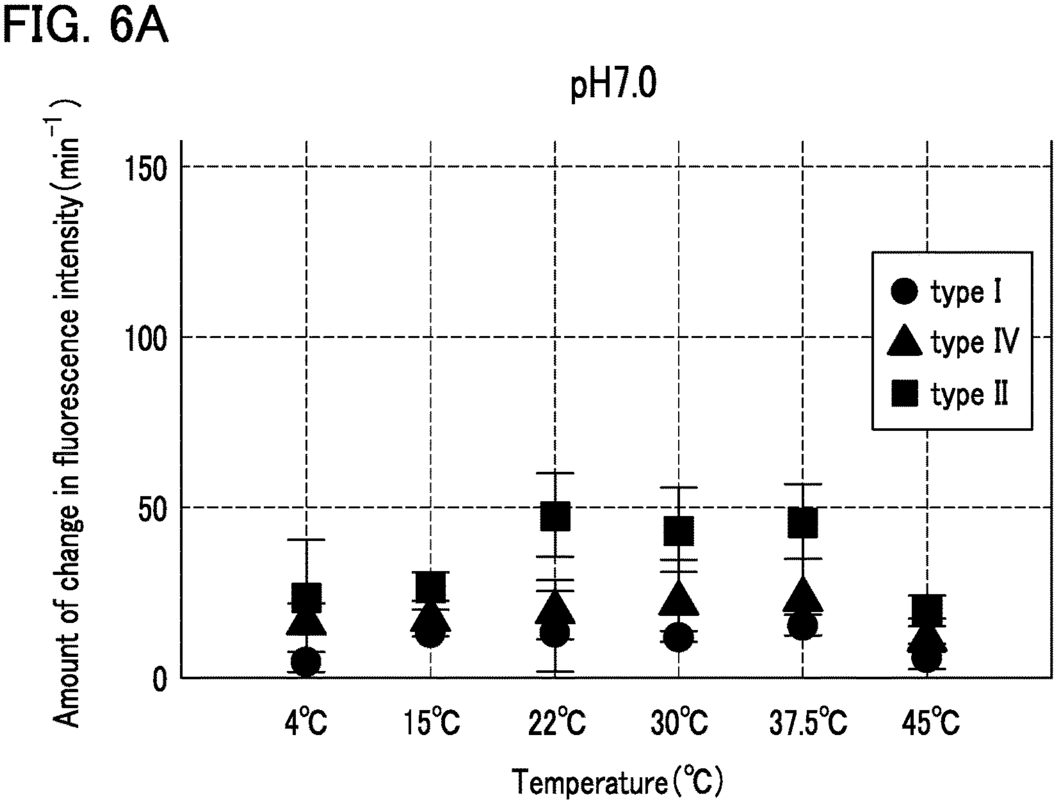
FIG. 6A is a diagram illustrating a result of fluorescence measurement of a liquid sample (pH 7.0) in which a bacterial body has been subjected to enzyme reaction at different temperatures.
Figure 6B:
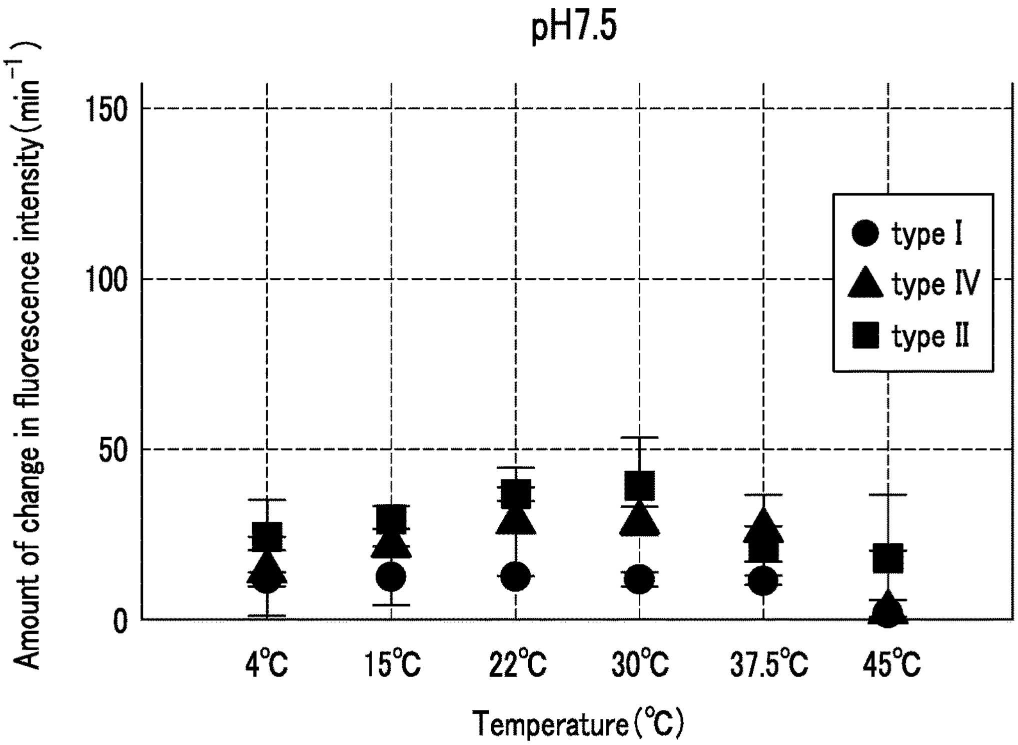
FIG. 6B is a diagram illustrating a result of fluorescence measurement of a liquid sample (pH 7.5) in which a bacterial body has been subjected to enzyme reaction at different temperatures.
Figure 6C:
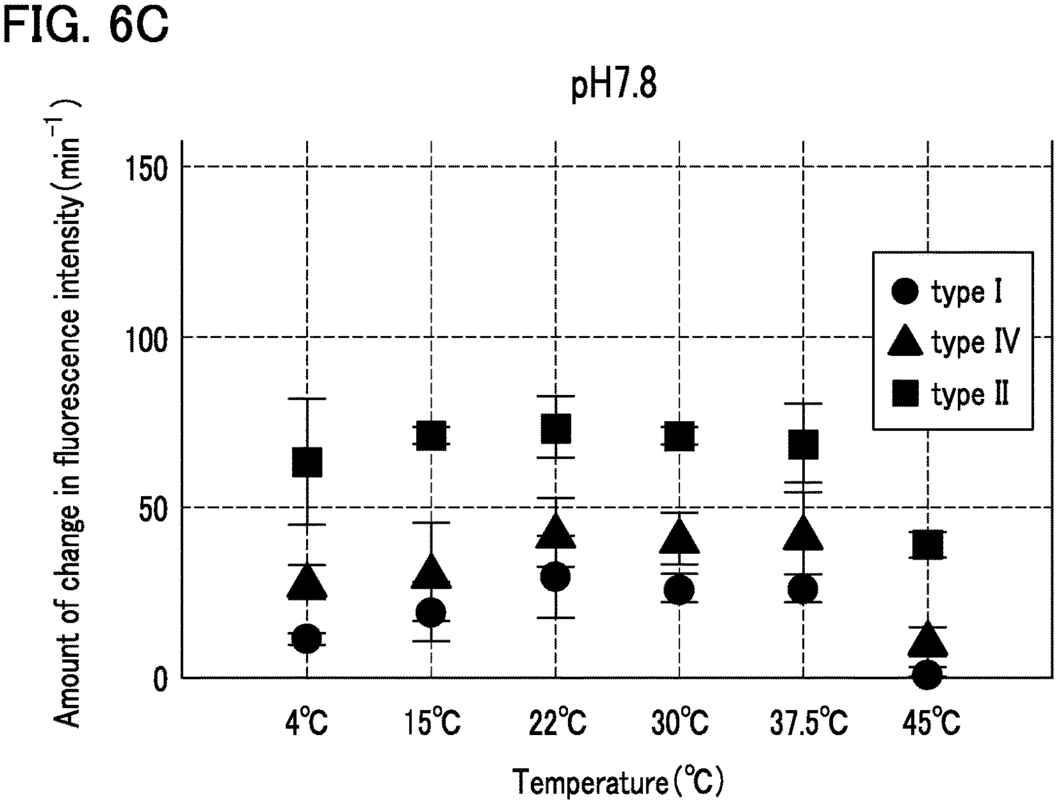
FIG. 6C is a diagram illustrating a result of fluorescence measurement of a liquid sample (pH 7.8) in which a bacterial body has been subjected to enzyme reaction at different temperatures.
Figure 6D:
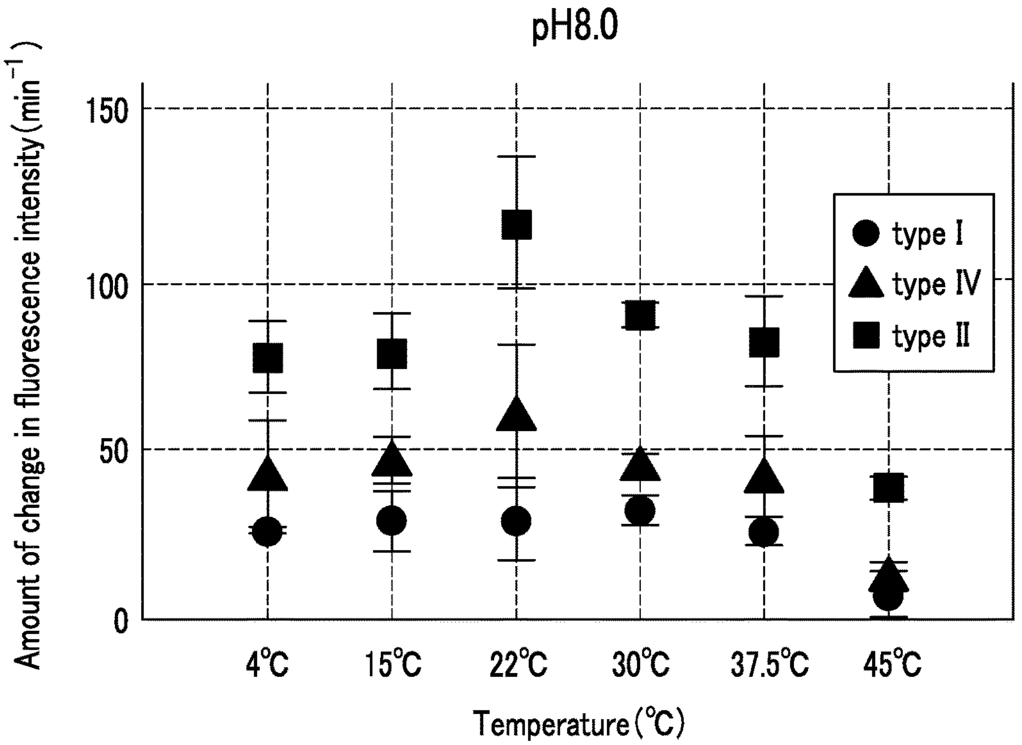
FIG. 6D is a diagram illustrating a result of fluorescence measurement of a liquid sample (pH 8.0) in which a bacterial body has been subjected to enzyme reaction at different temperatures.

FIG. 6A to FIG. 6E are each a diagram illustrating a result of a fluorescence measurement of a liquid sample in which a bacterial body has been subjected to enzyme reaction at different temperatures. FIG. 6A illustrates a result under a condition of the enzyme reaction at pH 7.0; FIG. 6B, at pH 7.5; FIG. 6C, at pH 7.8; FIG. 6D, at pH 8.0; and, FIG. 6E, at pH 8.5.

FIG. 6A to FIG. 6E each illustrate the result obtained by: separating a cell suspension liquid of Pg bacteria by centrifugalization; collecting a deposit therefrom; preparing a liquid sample to which the deposit containing the bacteria is added; adjusting a pH of the liquid sample to an appropriate pH condition; subjecting the liquid sample to enzyme reaction; and measuring a fluorescence intensity of the liquid sample using a fluorescence measurement device.

In each of FIG. 6A to FIG. 6E, the abscissa represents a temperature [° C.] of the liquid sample, and the ordinate represents an amount of change over time in fluorescence intensity. The amount of change over time in fluorescence intensity is obtained by: measuring a fluorescence after starting the enzyme reaction; and converting the measured result into an amount of change per one minute. In the figures, each of plots with • represents a result of the strain 33277 whose genotype of the fimA gene is type I; with ■, the strain TDC 60, type II; and, with ♦, the strain W83, type IV.

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for the each strain is three.

As illustrated in FIG. 6A, under a condition at pH 7.0, the amounts of change over time in fluorescence intensity for each of the genotypes have values similar to each other at temperatures of 4° C. to 15° C. and 45° C. In the meantime, at 22° C. to 37.5° C., the amounts of change over time of type I and type IV have values similar to each other, while those of type II are higher than those of type I or type IV.

As illustrated in FIG. 6B, at pH 7.5, the amounts of change over time in fluorescence intensity for each of the genotypes have values similar to each other at temperatures of 4° C. to 15° C. and 37.5° C. to 45° C. In the meantime, at 22° C. to 30.0° C., the amounts of type II or type IV is slightly higher than that of type I with a difference therebetween not so large.

As illustrated in FIG. 6C, at pH 7.8, the amounts of change over time in fluorescence intensity of type I are mostly higher at 22° C. to 37.5° C. than those at 4° C. to 15° C. or 45° C. At 4° C. to 45° C., the amounts of change over time of type IV: are mostly higher than those of type I; and, especially at 4° C. or 30° C., are significantly higher than those of type I. At 4° C. to 45° C., the amounts of change over time of type II are significantly higher than those of type I and type IV.

As illustrated in FIG. 6D, at pH 8.0, the amounts of change over time of type I are mostly lower at 37.5° C. to 45° C. than those at 4° C. to 30° C. At 4° C. to 45° C., the amounts of change over time of type IV: are mostly higher than those of type I; and, especially at 15° C. to 37.5° C., are significantly higher than those of type I. At 4° C. to 45° C., the amounts of change over time of type II: are significantly higher than those of type I and type IV; and, at 22° C., are notably high, representing a local maximal value.

Figure 6E:
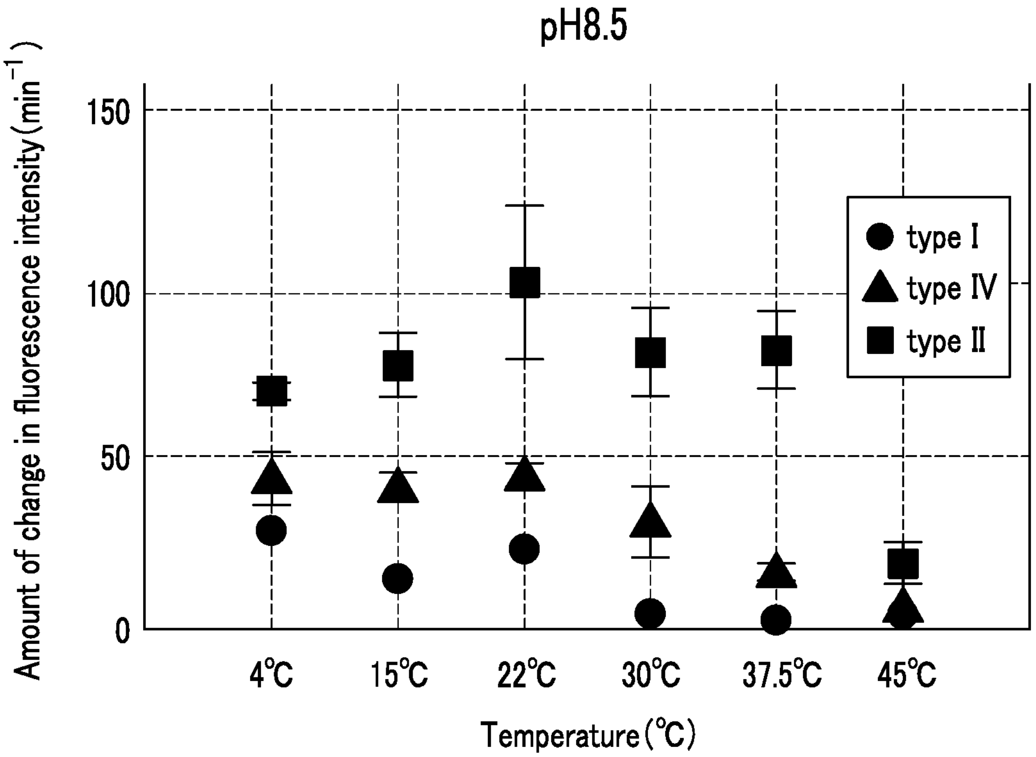
FIG. 6E is a diagram illustrating a result of fluorescence measurement of a liquid sample (pH 8.5) in which a bacterial body has been subjected to enzyme reaction at different temperatures.

As illustrated in FIG. 6E, at pH 8.5, the amounts of change over time of type I are mostly lower at 30° C. to 45° C. than those at 4° C. to 22° C. The amounts of change over time of type IV: are mostly higher than those of type I at 4° C. to 37.5° C.; and, especially at 15° C. to 37.5° C., are significantly higher than those of type I. At 4° C. to 45° C., the amounts of change over time of type II: are significantly higher than those of type I and type IV; and, at 15° C. to 37.5° C., are notably higher than those of type I and type IV.

It is demonstrated from the results shown in FIG. 6A to FIG. 6E that, when an enzyme-including bacterial body is subjected to enzyme reaction in a liquid sample in which a pH value is controlled at higher than pH 7.5 and not higher than pH 8.5 and a temperature is controlled at 4° C. to 45° C., the fluorescence intensity of type II becomes higher than that of type I or type IV. This can make accuracy in distinguishing between type II and type I or type IV higher. It is also demonstrated therefrom that, when the bacterial body is subjected to enzyme reaction in a liquid sample in which a pH value is controlled at higher than pH 7.8 and not higher than pH 8.5 and a temperature is controlled at 15° C. to 37.5° C., the fluorescence intensity of type VI becomes stronger than that of type I. This can make accuracy in distinguishing between type IV and type I or type II higher. That is, at 15° C. to 37.5° C., type I, type II, and type V can be distinguished from each other with high accuracy.

Figure 7A:
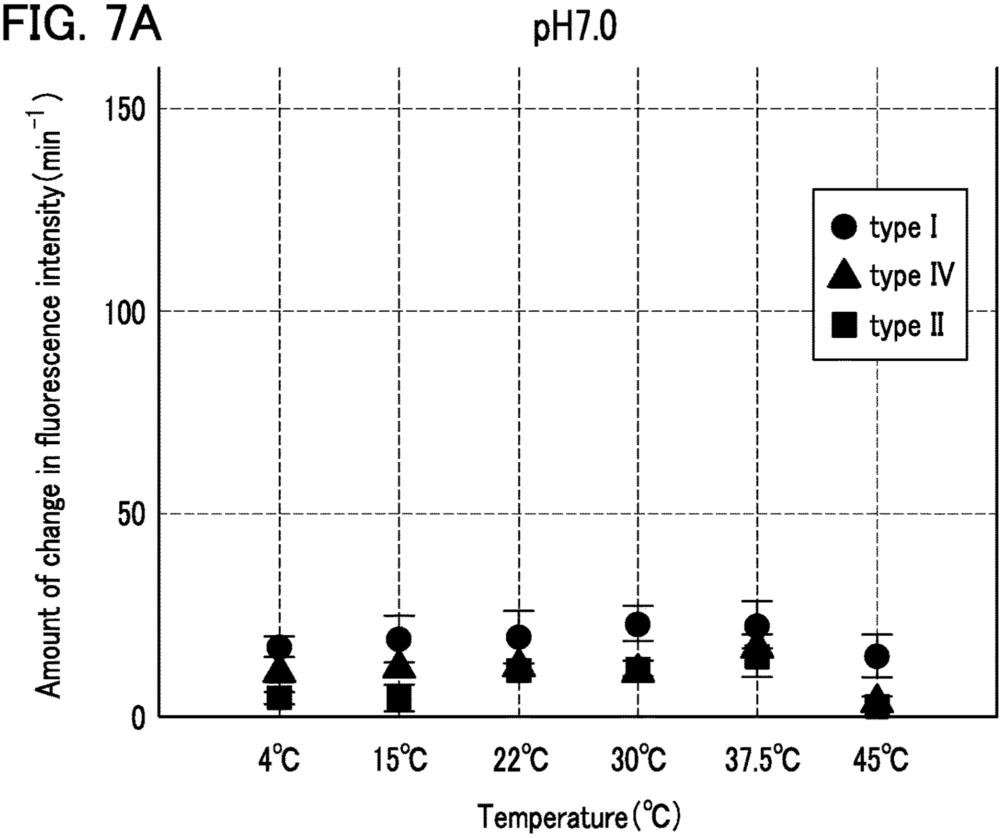
FIG. 7A is a diagram illustrating a result of fluorescence measurement of a liquid sample (pH 7.0) in which a bacterial body-based extractive matter has been subjected to enzyme reaction at different temperatures.
Figure 7B:
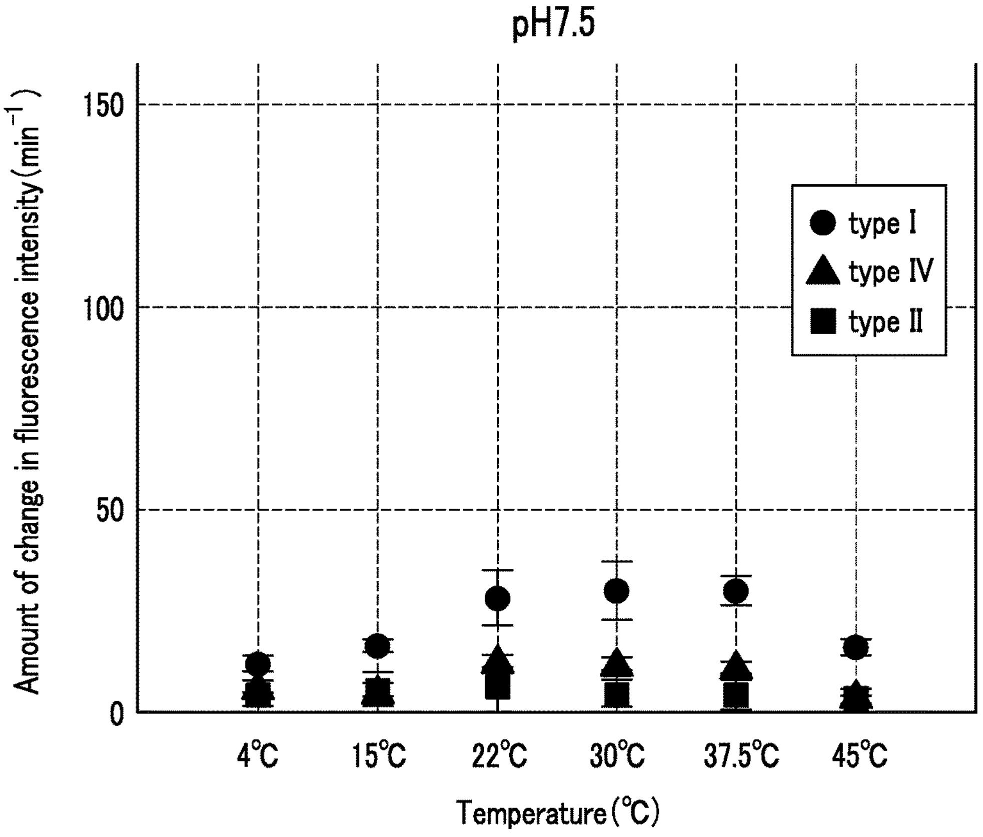
FIG. 7B is a diagram illustrating a result of fluorescence measurement of a liquid sample (pH 7.5) in which a bacterial body-based extractive matter has been subjected to enzyme reaction at different temperatures.
Figure 7C:
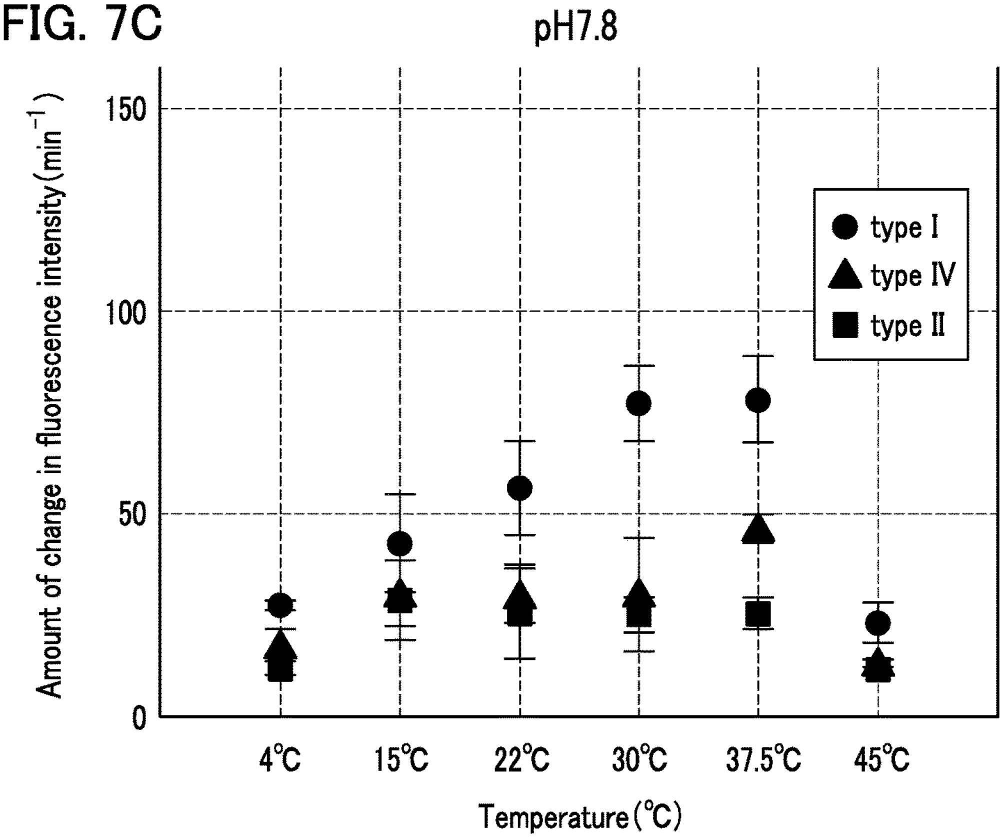
FIG. 7C is a diagram illustrating a result of fluorescence measurement of a liquid sample (pH 7.8) in which a bacterial body-based extractive matter has been subjected to enzyme reaction at different temperatures.
Figure 7D:
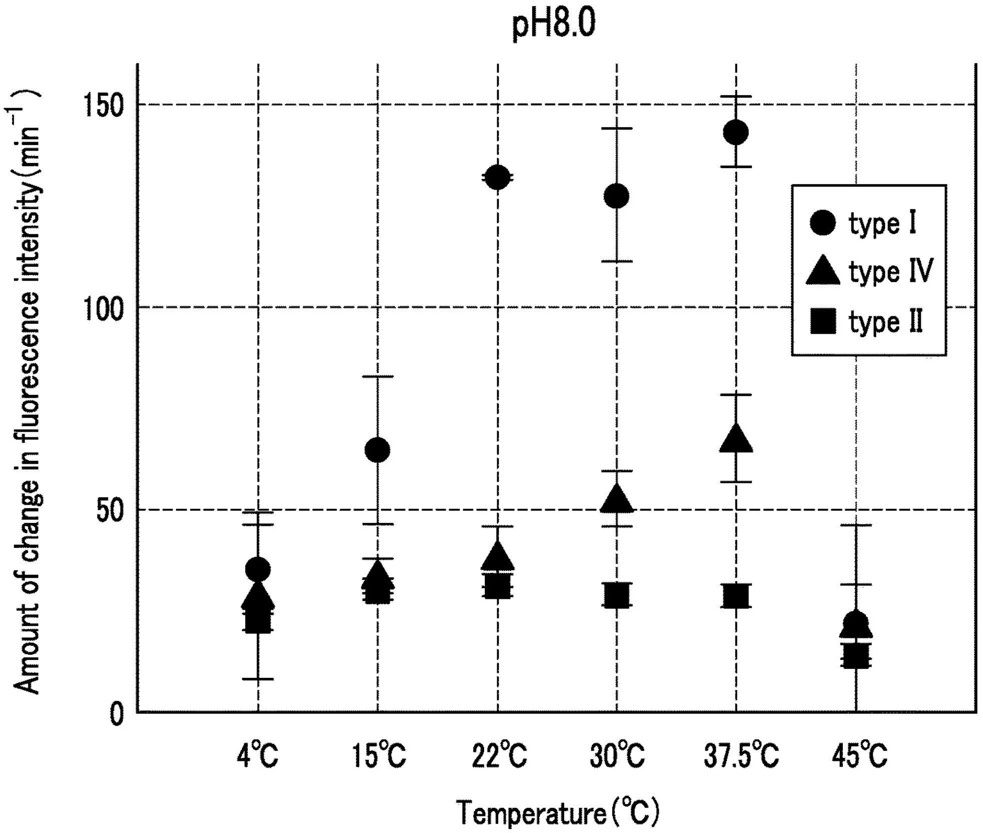
FIG. 7D is a diagram illustrating a result of fluorescence measurement of a liquid sample (pH 8.0) in which a bacterial body-based extractive matter has been subjected to enzyme reaction at different temperatures.

FIG. 7A to FIG. 7E are each a diagram illustrating a result of a fluorescence measurement of a liquid sample in which a bacterial body-based extractive matter has been subjected to enzyme reaction at different temperatures. FIG. 7A illustrates a result under a condition of the enzyme reaction at pH 7.0; FIG. 7B, at pH 7.5; FIG. 7C, at pH 7.8; FIG. 7D, at pH 8.0; and, FIG. 7E, at pH 8.5.

FIG. 7A to FIG. 7E each illustrate the result obtained by: separating a cell suspension liquid of Pg bacteria for each of the genotypes, by centrifugalization; collecting supernatant therefrom; preparing a liquid sample to which the supernatant as a bacterial body-based extractive matter of the bacteria is added; adjusting a pH of the liquid sample to an appropriate pH condition; subjecting the liquid sample to enzyme reaction at each of different temperature conditions; and measuring a fluorescence intensity of the liquid sample using a fluorescence measurement device.

In each of FIG. 7A to FIG. 7E, the abscissa represents a temperature [° C.] of the liquid sample, and the ordinate represents an amount of change over time in fluorescence intensity per one minute. The amount of change over time in fluorescence intensity is obtained by: measuring a fluorescence after starting the enzyme reaction; and converting the measured result into an amount of change per one minute. In the figures, each of plots with • represents a result of the strain 33277 whose genotype of the fimA gene is type I; with ■, the strain TDC 60, type II; and, with ♦, the strain W83, type IV.

The fluorescently-labeled substrate used herein is isobutyloxycarbonyl-glycyl-glycyl-L-arginyl-4-methylcoumaryl-7-amide (iBoc-Gly-Gly-Arg-MCA). The number of the liquid samples for the each strain is three.

As illustrated in FIG. 7A, under a condition at pH 7.0, the amounts of change over time in fluorescence intensity for each of the genotypes have values similar to each other at temperatures of 4° C. to 22° C. and 37.5° C. In the meantime, at 30° C. to 45° C., the amounts of change over time of type IV and type II have values similar to each other, while those of type I are higher than those of type IV or type II.

As illustrated in FIG. 7B, at pH 7.5, the amounts of change over time of type IV are mostly higher than those of type II at temperatures of 22° C. to 37.5° C. Especially at 30° C., the amounts of type IV are notably higher than those of type II. In the meantime, at 15° C. to 45° C., the amounts of type I are significantly higher than those of type IV and type II.

As illustrated in FIG. 7C, at pH 7.8, the amounts of change over time in fluorescence intensity of type I are mostly higher at 15° C. to 37.5° C. than those at 4° C. or 45° C. At 22 C to 37.5° C., the amounts of change over time of type IV: are mostly higher than those of type II; and, especially at 37.5° C., are significantly higher than those of type II. At 15° C. to 45° C., the amounts of change over time of type I: are significantly higher than those of type IV and type II; and, at 30° C. to 37.5° C., are notably higher than those of type IV and type II.

As illustrated in FIG. 7D, at pH 8.0, the amounts of change over time of type II are lower at 45° C. than those at 4° C. to 37.5° C. At 22° C. to 37.5° C., the amounts of change over time of type IV are higher than those of type II. Especially at 30° C. to 37.5° C., the amounts of change over time of type IV are significantly higher than those of type II. At 15° C. to 37.5° C., the amounts of change over time of type I: are significantly higher than those of type IV and type II; and, at 22° C. to 37.5° C., are notably higher than those of type IV and type II.

Figure 7E:
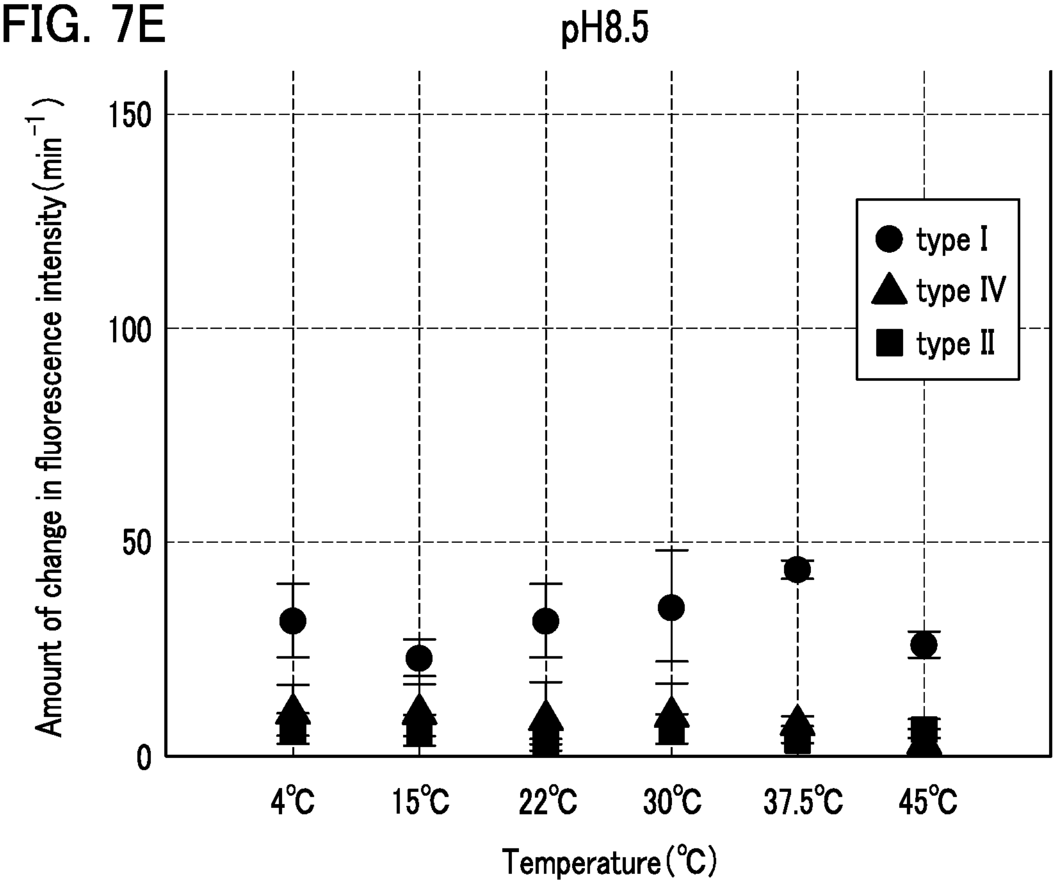
FIG. 7E is a diagram illustrating a result of fluorescence measurement of a liquid sample (pH 8.5) in which a bacterial body-based extractive matter has been subjected to enzyme reaction at different temperatures.

As illustrated in FIG. 7E, at pH 8.5, the amounts of change over time of type II and type IV values are similar to each other at 4° C. to 45° C. At 4° C. to 45° C., the amounts of change over time of type I: are significantly higher than those of type IV and type II; and, especially at 37.5° C., are notably higher than those of type IV or type II.

It is demonstrated from the results illustrated in each of FIG. 7A to FIG. 7E that, when a bacterial body-based extractive matter in which an enzyme is produced is subjected to enzyme reaction in a liquid sample in which a pH value is controlled at higher than pH 7.5 and not higher than pH 8.5 and a temperature is controlled in a temperature range from 15° C. to 45° C., a fluorescence intensity of type I is higher than that of type IV or type II. This can obtain a higher accuracy in distinguishing between type I and type IV or type II. It is also demonstrated therefrom that, when the bacterial body is subjected to enzyme reaction in a liquid sample in which a pH value is controlled at not lower than pH 7.5 and not higher than pH 8.0 and a temperature is controlled in a temperature range from 30° C. to 37.5° C., the fluorescence intensity of type VI becomes higher than that of type II. This can obtain a higher accuracy in distinguishing between type IV and type I or type II.

Figure 8:
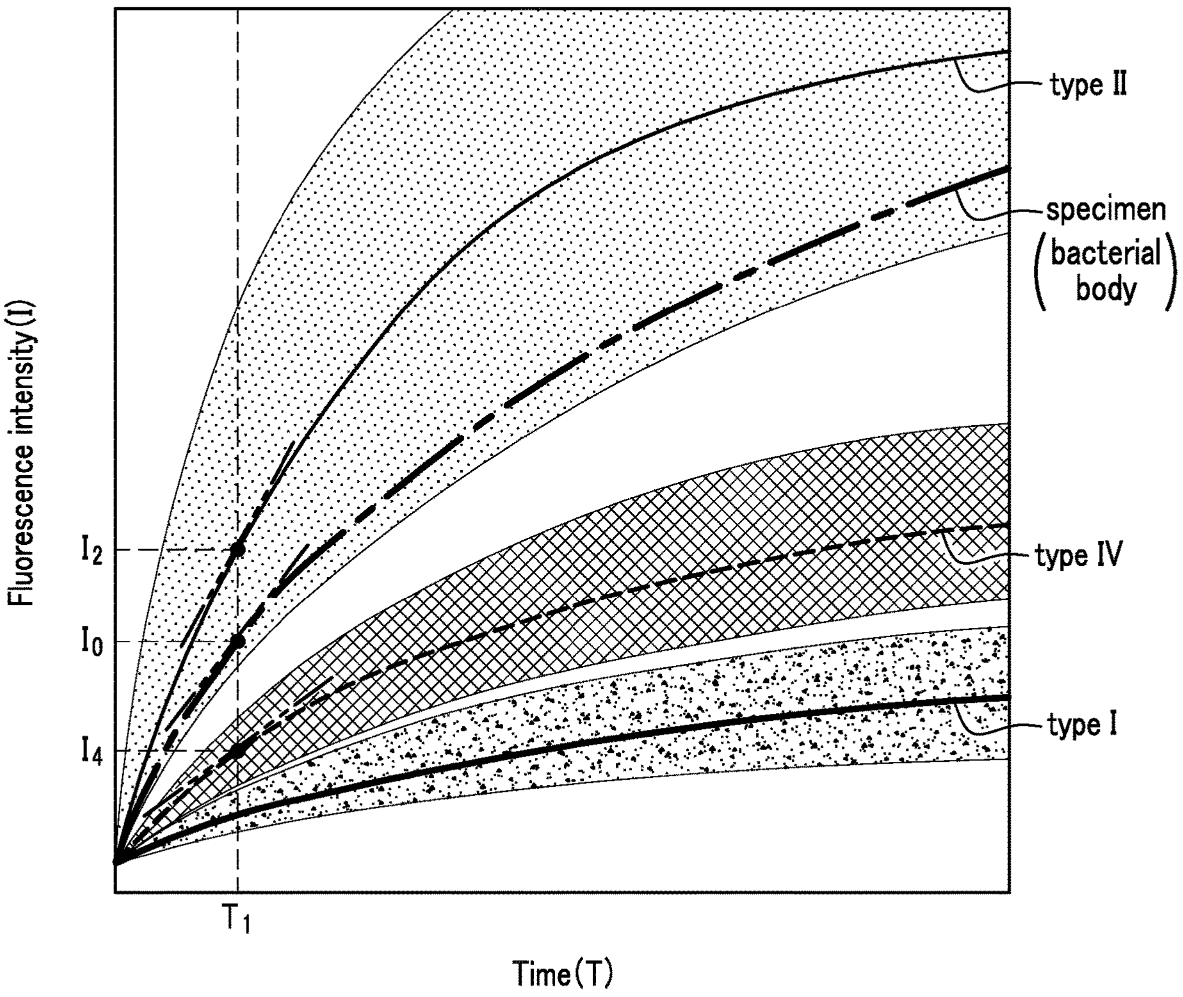
FIG. 8 is a diagram for explaining how a genotype of a microorganism responsible for periodontal disease is determined using a bacterial body thereof.

FIG. 8 is a diagram for explaining how a genotype of the microorganism responsible for periodontal disease using a bacterial body thereof is determined.

In FIG. 8. the abscissa represents a time starting at a beginning of enzyme reaction, and the ordinate represents a fluorescence intensity. The dash-dot-dash lines in the figure represents a specific example of fluorescence intensity of a liquid sample containing a bacterial body of the microorganism responsible for periodontal disease, whose genotype is not yet known (a specimen).

In the figure, the thick solid line represents a specific example of representative values of the fluorescence intensity obtained by Pg bacteria whose genotype is type I; the thin solid line, type II; and, the dashed line, type IV.

As illustrated in FIG. 8, when fluorescence in the liquid samples each containing a bacterial body of the microorganism responsible for periodontal disease whose genotype is already known are measured, if the different liquid samples have, depending on different genotypes: different enzyme activities of the microorganism responsible for periodontal disease; capacities to produce or secrete enzymes extracellularly; or the like, then the detected intensities are found to be different fluorescence according to the different genotypes. Fluorescence of a large number of liquid samples whose genotypes are already known are measured and subjected to regression analysis or any other appropriate analysis. The result demonstrates that, as indicated by the curved lines (lines of type I, type II, and type IV) in the figure, representative values in groups for each of the genotypes can be obtained. The measurement values of the fluorescence intensity in the groups each exhibit a distribution in a prescribed distance range from the respective curved lines (the lines of type I, type II, and type IV) and form respective measurement groups (clusters) for each of the genotypes (see the shaded areas in the figure).

In the meantime, when fluorescence in a liquid sample containing a bacterial body of the microorganism responsible for periodontal disease, whose genotype is not yet known, is measured, as indicated by the dash-dot-dash line in the figure, the resultant measurement values are those close to any of the curved lines (the lines of type I, type II, and type IV) of the representative values of the respective different genotypes. FIG. 8 illustrates an example of the measurement result in which the curved line of the unknown genotype is close to the line of type II. Such a measurement result can be obtained because a specimen collected from a subject is in a state in which any one of the genotypes is dominant and has an enzyme activity or a capacity to extracellularly produce or secrete enzymes similar to that of the dominant genotype.

This means that a genotype of a specimen can be determined by: when a prescribed reaction time has passed after starting an enzyme reaction (for example, time $T_1$), measuring a fluorescence intensity of each of liquid samples; and comparing a fluorescence intensity value of a liquid sample containing a bacterial body of the microorganism responsible for periodontal disease, whose genotype is not yet known, (for example, a fluorescence intensity $I_0$), with a fluorescence intensity value of another liquid sample containing a bacterial body of the microorganism responsible for periodontal disease, whose genotype is already known, (for example, fluorescence intensities 12, 14 or a boundary line of a shaded area in the figure), per the same period of reaction time.

In comparing an experimental area containing a specimen for a bacterial body of a microorganism responsible for periodontal disease, whose genotype is not yet known, with a control area containing that whose genotype is already known, though it is necessary to use the same enzyme reaction conditions and measuring systems of the fluorescence measurement, the determination method described above allows a genotype of a specimen to be determined, by simply comparing respective fluorescence intensity values.

Alternatively, a genotype of a specimen can be determined by: measuring a fluorescence intensity of each of liquid samples at prescribed regular intervals after starting an enzyme reaction (for example, an infinitesimal section near time $T_1$); calculating an amount of change over time in fluorescence intensity (a slope), which is a temporal differentiation thereof; and comparing an amount of change over time in fluorescence intensity in a liquid sample containing a bacterial body of the microorganism responsible for periodontal disease, whose genotype is not yet known (for example, a slope of a tangent line at a point of intersection $T_1$-$I_0$), with an amount of change over time in another liquid sample, whose genotype is already known (for example, a slope of a tangent line at a point of intersection of $T_1$-$I_2$, a slope of a tangent line at a point of intersection of $T_1$-$I_4$, or a slope of a tangent line of a boundary line of the shaded area in the figure).

When the determination method described above is used, though it is required to calculate an amount of change over time (a slope), an accurate comparison can be made. This is because usage of one and the same time of enzyme reaction is not indispensable and a measurement systematic error in a result of fluorescence measurement does not easily occur. Note that amounts of change over time in fluorescence intensity (slopes) can be compared with each other per reaction time or between the maximum values in the course of the enzyme reaction.

Figure 9:
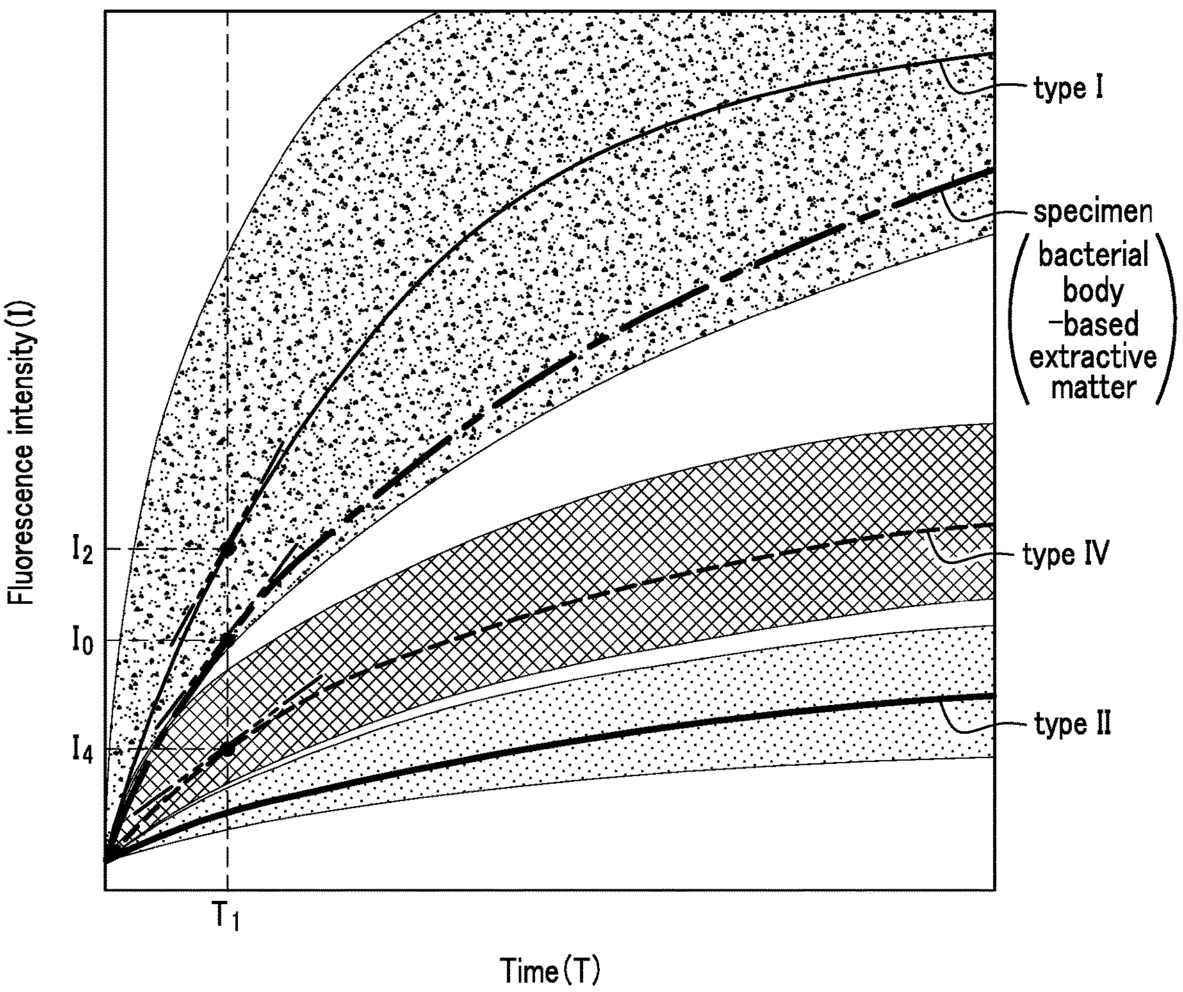
FIG. 9 is a diagram for explaining how a genotype of the microorganism responsible for periodontal disease is determined using a bacterial body-based extractive matter thereof.

FIG. 9 is a diagram for explaining how a genotype of the microorganism responsible for periodontal disease using a bacterial body-based extractive matter thereof is determined.

In FIG. 9, the abscissa represents a time starting at a beginning of enzyme reaction, and the ordinate represents a fluorescence intensity. The dash-dot-dash line in the figure represents a specific example of fluorescence intensity of a liquid sample containing a bacterial body-based extractive matter of the microorganism responsible for periodontal disease, whose genotype is not yet known (a specimen).

In the figure, the thick solid line represents a specific example of representative values of the fluorescence intensity obtained by Pg bacteria whose genotype is type II; the thin solid line, type I; and, the dashed line, type IV.

As illustrated in FIG. 9, when fluorescence in the liquid samples each containing the bacterial body-based extractive matter of the microorganism responsible for periodontal disease, whose genotype is already known, are measured, if the different liquid samples have different enzyme activities of the microorganism responsible for periodontal disease, depending on different genotypes, then, as in the case of using a bacterial body (see FIG. 8), the detected fluorescence intensities are different according to the different genotypes. When a bacterial body-based extractive matter is used, however, an influence thereof on a capacity to extracellularly produce or secrete enzymes becomes small. The measurement values of the fluorescence intensity for each of the genotypes therefore exhibit a trend different from that using a bacterial body.

Meanwhile, when fluorescence in a liquid sample containing a bacterial body-based extractive matter extracted from the microorganism responsible for periodontal disease, whose genotype is not yet known, is measured, as indicated by the dash-dot-dash line in the figure, the resultant measurement values are those close to any of the curved lines (lines of type I, type II, and type IV) of representative values of respective different genotypes. When the bacterial body-based extractive matter is used, compared with a case when a bacterial body is used, because the fluorescence intensity of type I and that of type II are inversely correlated, the smaller a measurement value of fluorescence intensity, the closer to the curve line of type II, and, the larger the measurement value of fluorescence intensity, the closer to the curve line of type I.

This means that, when a bacterial body-based extractive matter is used, as in the case of using a bacterial body (see FIG. 8), a genotype of a specimen can be determined by: when a prescribed reaction time has passed after starting an enzyme reaction (for example, time $T_1$), measuring a fluorescence intensity of each of liquid samples; and comparing a fluorescence intensity value of a liquid sample containing a bacterial body-based extractive matter extracted from the microorganism responsible for periodontal disease, whose genotype is not yet known, (for example, a fluorescence intensity $I_0$), with a fluorescence intensity value of another liquid sample containing a bacterial body-based extractive matter of the microorganism responsible for periodontal disease, whose genotype is already known, (for example, fluorescence intensities 12, 14 or a boundary line of the shaded area in the figure), per the same period of reaction time.

Alternatively, a genotype of a specimen can be determined by: measuring a fluorescence intensity of each of liquid samples at prescribed regular intervals after starting an enzyme reaction over time (for example, an infinitesimal section near time $T_1$); calculating an amount of change over time in fluorescence intensity (a slope), which is a temporal differentiation thereof; and comparing an amount of change over time in fluorescence intensity of a liquid sample containing a bacterial body-based extractive matter of the microorganism responsible for periodontal disease, whose genotype is not yet known (for example, a slope of a tangent line at a point of intersection $T_1$-$I_0$), with an amount of change over time in another liquid sample, whose genotype is already known (for example, a slope of a tangent line at a point of intersection of $T_1$-$I_2$, a slope of a tangent line at a point of intersection of $T_1$-$I_4$, or a slope of a tangent line of a boundary line of the shaded area in the figure).

In the genotype determination step S30, for example, a genotype of interest is determined by: preparing two different liquid samples, that is, a liquid sample of an experimental area composed of a microorganism responsible for periodontal disease or that containing a bacterial body-based extractive matter thereof (a specimen), whose genotype is not yet known, and another liquid sample of a control area composed of the microorganism responsible for periodontal disease or that containing a bacterial body-based extractive matter thereof, whose genotype is already known; and comparing a result of fluorescence measurement of the liquid sample of the experimental area with that of the control area. Note that, more specifically, before the results of the fluorescence measurement are obtained, based on which the determination is made, the liquid sample of the experimental area and that of the control area are prepared to substantially satisfy the same conditions such as a pH, a temperature, an amount of a specimen of a microorganism responsible for periodontal disease or a bacterial body-based extractive matter thereof, and a concentration of a fluorescently-labeled substrate; and are then subjected to enzyme reaction.

The number of liquid samples composing a control area can be any number not less than one and is preferably but not necessarily a large number. The control area may include: a liquid sample containing the microorganism responsible for periodontal disease or a bacterial body-based extractive matter thereof, whose genotype is already known; and a liquid sample containing a microorganism responsible for periodontal disease or a bacterial body-based extractive matter thereof, whose genotype is not yet known. In terms of a secure determination of a genotype, the control area is preferably but not necessarily composed of only a liquid sample containing the microorganism responsible for periodontal disease or a bacterial body-based extractive matter thereof, whose genotype is already known.

The control area may contain, as a microorganism responsible for periodontal disease, whose genotype is already known, or a bacterial body-based extractive matters thereof: bacterial bodies or bacterial body-based extractive matters thereof of a single genotype; or those of a plurality of types of genotypes. For example, when the control area contains those of type I only, whether or not a bacteria specimen is of type I can be determined. When the control area contains those of type I to type V, of which genotype a specimen is can be determined.

The control area can be prepared by, for example, using, as a microorganism responsible for periodontal disease, whose genotype is already known, or a bacterial body-based extractive matter thereof: a bacterial body or a bacterial body-based extractive matter thereof of a strain whose genotype has been previously determined by a fluorometric method; a bacterial body or a bacterial body-based extractive matter thereof of a deposited strain or an isolated strain which is generally available by distribution; or the like.

Some of specific examples of the deposited strain or the isolated strain include: a strain ATCC_33277 and a strain ATCC_BAA-1703 (FDC 381) whose fimA gene is of type I; a strain JCM_19600 (TDC 60), a strain 275 (strain HG184), and a strain 268, type II; a strain ATCC_49417 (RB22D-1), type III; a strain ATCC_BAA-308 (W83) and a strain ATCC_53978 (W50), type IV; and a strain HNA99, type V.

A liquid sample whose fluorescence is to be measured is preferably but not necessarily subjected to enzyme reaction with a pH value thereof adjusted to higher than pH 7.5 and not higher than pH 8.5, before the fluorescence measurement. The pH value of the liquid sample is preferably not lower than pH 7.8. The pH value of the liquid sample is also preferably not higher than pH 8.4; more preferably, not higher than pH 8.3; further preferably, not higher than pH 8.2; and still further preferably, not higher than pH 8.1. When the pH value is controlled as described above, a genotype of the fimA gene of Pg bacteria can be determined more accurately.

The liquid sample whose fluorescence is to be measured is preferably but not necessarily subject to a fluorescence measurement at a constant temperature controlled at a prescribed temperature. The temperature of the liquid sample is preferably but not necessarily, not lower than 4° C. and not higher than 45° C. When a bacterial body-based extractive matter is used, the temperature of the liquid sample is preferably not lower than 25° C.; more preferably, not lower than 30° C.; further preferably, not lower than 34° C.; and, still further preferably not lower than 36° C. Also in that case, the temperature of the liquid sample is preferably not higher than 40° C.; more preferably, not higher than 39° C.; and, further preferably, not higher than 38° C. Meanwhile, when a bacterial body is used, a temperature of a liquid sample is preferably not lower than 4° C.; more preferably, not lower than 10° C.; further preferably, not lower than 15° C.; still further preferably not lower than 18° C.; and, yet further preferably not lower than 21° C. Also in that case, the temperature of the liquid sample is preferably not higher than 37° C.; more preferably, not higher than 30° C.; further preferably, not higher than 26° C.; and, yet further preferably, not higher than 23° C. When the temperature is controlled as described above, a genotype of the fimA gene of Pg bacteria can be determined more accurately.

Comparison between a result of a fluorescence measurement of the experimental area and that of the control area can be made by, more specifically, comparing: a value of fluorescence intensity or an amount of change over time of fluorescence intensity of a liquid sample containing a microorganism responsible for periodontal disease or a bacterial body-based extractive matter thereof (a specimen) measured in the experimental area, whose genotype is not yet known; with a value of fluorescence intensity or an amount of change over time of fluorescence intensity of a liquid sample containing a microorganism responsible for periodontal disease or a bacterial body-based extractive matter thereof (a specimen) measured in the control area, whose genotype is already known, respectively. That is, the two values of fluorescence intensity or the two amounts of change over time of fluorescence intensity are compared therebetween.

As a result of the comparison between the result of the fluorescence measurement in the experimental area and that in the control area, if the value of fluorescence intensity or the amount of change over time of fluorescence intensity of the liquid sample containing the microorganism responsible for periodontal disease or the bacterial body-based extractive matter thereof (the specimen) measured in the experimental area, whose genotype is not yet known, is the same as or similar to the value of fluorescence intensity or the amount of change over time of fluorescence intensity of the liquid sample containing the microorganism responsible for periodontal disease or a bacterial body-based extractive matter thereof (the specimen) measured in the control area, whose genotype is already known, then a genotype of a fimA gene of the microorganism responsible for periodontal disease of the liquid sample in the experimental area can be determined to be the same as that in the control area, whose genotype is already known.

Meanwhile, as a result of the comparison between the result of the fluorescence measurement in the experimental area and that in the control area, if the value of fluorescence intensity or the amount of change over time of fluorescence intensity of the liquid sample containing the microorganism responsible for periodontal disease or the bacterial body-based extractive matter thereof (the specimen) measured in the experimental area, whose genotype is not yet known, is neither the same nor similar to the value of fluorescence intensity or the amount of change over time of fluorescence intensity of the liquid sample containing the microorganism responsible for periodontal disease or the bacterial body-based extractive matter thereof (the specimen) measured in the control area, whose genotype is already known, then the genotype of the fimA gene of the microorganism responsible for periodontal disease of the liquid sample in the experimental area can be determined to be different from that in the control area, whose genotype is already known.

The comparison between a result of a fluorescence measurement in the experimental area and that in the control area can be made by, for example, comparing between respective measurement values as they are or between respective representative values such as average values. As another example, a value obtained by a measurement in an experimental area is compared with a representative value such as an average value obtained by a measurement in a control area. If a difference between the measurement value in the experimental area and the representative value in the control area is in a range of ±30% with respect to the representative value in the control area, then the two fluorescence measurement results can be determined to be approximate to each other.

In the genotype determination step S30, for example, a genotype of interest is determined by: preparing a group constituted by a plurality of liquid samples, which includes liquid samples each containing a microorganism responsible for periodontal disease or a bacterial body-based extractive matter thereof (a specimen), whose genotype is not yet known, and each targeted for determination of the genotype; and comparing respective results of fluorescence measurement of the liquid samples in the group with each other. Note that, more specifically, before the results of the fluorescence measurement are obtained, based on which the determination is made, the liquid samples each as a target or a non-target of the determination: are all prepared to substantially satisfy the same conditions such as a pH, a temperature, an amount of a specimen of the microorganism responsible for periodontal disease or the bacterial body-based extractive matter thereof, and a concentration of a fluorescently-labeled substrate; and are then subjected to enzyme reaction.

The number of liquid samples in the group can be any number not less than two and is preferably but not necessarily a large number. As long as the group of liquid samples include a liquid sample as a target for determination containing a microorganism responsible for periodontal disease or a bacterial body-based extractive matter thereof (a specimen), whose genotype is not yet known, the group of liquid samples may include liquid samples, all of which contain the microorganism responsible for periodontal disease or the bacterial body-based extractive matter thereof, whose genotype are not yet known. Alternatively, the group of liquid samples may include both: liquid samples each containing the microorganism responsible for periodontal disease or the bacterial body-based extractive matter thereof, whose genotype is already known; and liquid samples each containing the microorganism responsible for periodontal disease or the bacterial body-based extractive matter thereof, whose genotype is not yet known.

The group of liquid samples preferably but not necessarily includes strains or bacterial body-based extractive matters thereof of a plurality of genotypes, as the microorganisms responsible for periodontal disease and the bacterial body-based extractive matters thereof, whose genotype are already known. For example, when a control area contains those of type I to type V, a result of fluorescence measurement shows measurement value groups (clusters) of five different types depending on respective different genotypes which have respective different changes in fluorescence intensity over time. Similarity between a result of fluorescence measurement of a specimen and those of the groups of the measurement values is determined, which makes it possible to determine of which genotype the specimen is.

A pH value of a liquid sample whose fluorescence is to be measured is preferably but not necessarily adjusted to higher than pH 7.5 and not higher than pH 8.5 and is then subjected to enzyme reaction, before the fluorescence measurement. The pH value of the liquid sample is preferably not lower than pH 7.8. The pH value of the liquid sample is also preferably not higher than pH 8.4; more preferably, not higher than pH 8.3; further preferably, not higher than pH 8.2; and still further preferably, not higher than pH 8.1. When the pH value is controlled as described above, a genotype of the fimA gene of Pg bacteria can be determined more accurately.

The liquid sample whose fluorescence is to be measured is preferably but not necessarily subject to a fluorescence measurement at a constant temperature controlled at a prescribed temperature. The temperature of the liquid sample is preferably but not necessarily, not lower than 4° C. and not higher than 45° C. When a bacterial body-based extractive matter is used, the temperature of the liquid sample is preferably not lower than 25° C.; more preferably, not lower than 30° C.; further preferably, not lower than 34° C.; and, still further preferably not lower than 36° C. Also in that case, the temperature of the liquid sample is preferably not higher than 40° C.; more preferably, not higher than 39° C.; and, further preferably, not higher than 38° C. Meanwhile, when a bacterial body is used, a temperature of a liquid sample is preferably not lower than 4° C.; more preferably, not lower than 10° C.; further preferably, not lower than 15° C.; still further preferably not lower than 18° C.; and, yet further preferably not lower than 21° C. Also in that case, the temperature of the liquid sample is preferably not higher than 37° C.; more preferably, not higher than 30° C.; further preferably, not higher than 26° C.; and, yet further preferably, not higher than 23° C. When the temperature is controlled as described above, a genotype of the fimA gene of Pg bacteria can be determined more accurately.

The results of fluorescence measurement in a group of samples can be compared between, more specifically: a value of fluorescence intensity or an amount of change over time of fluorescence intensity of a target liquid sample containing a microorganism responsible for periodontal disease or a bacterial body-based extractive matter thereof, whose genotype is not yet known; and a group of measurement values, that is, values of fluorescence intensity or amounts of change over time of fluorescence intensity of a plurality of liquid samples in the group liquid samples. In that case, the values of fluorescence intensity therebetween or the amounts of change over time of fluorescence intensity therebetween are compared.

Let us assume a case in which: a bacterial body is used in preparing a liquid sample; and results of fluorescence measurement in a group of samples are compared therebetween. It is then demonstrated that, from among values of fluorescence intensity or amounts of change over time of fluorescence intensity of measurement values in the group constituted by a plurality of liquid samples measured, if a value of fluorescence intensity or an amount of change over time of fluorescence intensity of a liquid sample targeted for determination in the group, whose genotype is not yet known, is categorized into a measurement value group positioned uppermost, then a genotype of the fimA gene of the microorganism responsible for periodontal disease of the target liquid sample can be determined to be type II. In another case in which a bacterial body-based extractive matter is used in preparing a liquid sample, if a target liquid sample is categorized into a measurement value group positioned uppermost, then a genotype of the fimA gene of the microorganism responsible for periodontal disease of the target liquid sample can be determined to be type I.

The measurement values group positioned uppermost is a group of measurement values into which maximal values of fluorescence intensity are categorized from among all measurement value groups with all genotypes, as illustrated in FIG. 8 by dotted shading and in FIG. 9 by mottled shading. Similarly, the measurement value group positioned uppermost is a measurement value group into which maximal values of amounts of change over time of fluorescence intensity (slopes) are categorized. Thus, when: a bacterial body is used in preparing a liquid sample; and a group of liquid samples contain type II and type I or type IV, then the measurement value group positioned uppermost is determined to be of type II. On the other hand, when: a bacterial body-based extractive matter is used in preparing a liquid sample; and a group of liquid samples contains type I and type IV or type II, then the measurement value group positioned uppermost is determined to be of type I.

Let us assume a case in which a bacterial body or a bacterial body-based extractive matter thereof is used in preparing a liquid sample, results of fluorescence measurement of samples in a group (a measurement value group) are compared therebetween. It is then demonstrated that, from among measurement values of fluorescence intensity or amounts of change over time of fluorescence intensity of a plurality of liquid samples measured in the group, if a value of fluorescence intensity or an amount of change over time of fluorescence intensity of a liquid sample targeted for determination in the group, whose genotype is not yet known, is categorized into a measurement value group positioned second uppermost, then a genotype of the fimA gene of the microorganism responsible for periodontal disease of the liquid sample of interest can be determined to be of type IV.

The measurement value group positioned second uppermost is a group of measurement values into which second maximal values of fluorescence intensity are categorized from among all measurement value groups with all genotypes, as illustrated in each of FIG. 8 and FIG. 9 by cross shading. Similarly, the measurement value group positioned second uppermost is a group of measurement values into which second maximal values of amounts of change over time of fluorescence intensity (slopes) are categorized. Thus, when: a bacterial body is used in preparing a liquid sample; and a group of liquid samples contains type II and type IV or type I, then the measurement value group positioned second uppermost is determined to be of type IV. On the other hand, when: a bacterial body-based extractive matter is used in preparing a liquid sample; and the groups of liquid samples contain type I and type IV or type II, then the measurement value group positioned second uppermost is of type IV.

Assume a case in which a bacterial body is used in preparing a liquid sample, results of fluorescence measurement of samples in a group (a measurement value group) are compared therebetween. It is then demonstrated that, from among values of fluorescence intensity or amounts of change over time of fluorescence intensity of a plurality of liquid samples measured in the measurement value group, if a value of fluorescence intensity or an amount of change over time of fluorescence intensity of a liquid sample targeted for determination in the group, whose genotype is not yet known, is categorized into a measurement value group positioned downmost, then a genotype of the fimA gene of the microorganism responsible for periodontal disease (a bacteria specimen) of the target liquid sample can be determined to be type I. On the other hand, when a bacterial body-based extractive matter is used in preparing a liquid sample, a genotype of the fimA gene of the microorganism responsible for periodontal disease of the target liquid sample categorized into the measurement value group positioned downmost is determined to be type II.

The measurement value group positioned downmost is a group of measurement values into which minimal values of fluorescence intensity are categorized from among all groups of measurement values with all genotypes, as illustrated in each of FIG. 8 and FIG. 9 by cross shading. Similarly, the measurement value group positioned downmost is a group of measurement values into which minimal values of amounts of change over time of fluorescence intensity (slopes) are categorized. Thus, when: a bacterial body is used in preparing a liquid sample; and a group of liquid samples contains type I and type II or type IV, then the measurement value group positioned downmost is determined to be of type I. On the other hand, when a bacterial body-based extractive matter is used in preparing a liquid sample, if a group of liquid samples contains type II and type IV or type I, then the measurement value group positioned downmost is determined to be of type II.

The results of fluorescence measurement in the group of liquid samples can be compared based on, for example, similarity between results obtained by the measurement. For example, when a measurement value obtained by measuring an experimental area is compared with that in a control area, if the measurement value in the experimental area falls within a prescribed range of similarity with respect to a group of measurement values in the control area, then the respective results of fluorescence measurement in the two areas can be deemed as similar to each other.

Measurement value groups in the control area may be previously classified for each genotype (clustering) and may be then compared with measurement values in the experimental area. The classification for each genotype can be performed by using a method of classifying measurement values for each genotype with a prescribed threshold, Ward's method, group average method, furthest neighbor method, shortest distance method, or any other calculation techniques of various types. Results of fluorescence measurement can be compared with each other, using various mathematical distances such as Euclidean distance.

When an enzyme activity of a microorganism responsible for periodontal disease has correlation with a genotype thereof, the determination method according to the present embodiment described above can determine the genotype of the microorganism responsible for periodontal disease, based on the enzyme activity obtained by the fluorometric method. Unlike the conventionally-used molecular biology technique, the determination method according to the embodiment can make the determination, taking into account an enzyme activity which advances the periodontal disease. This allows the determination of a genotype to be met with an actual pathological condition. Additionally, when a bacterial body is used in preparing a liquid sample, the determination method according to the embodiment makes it possible to use a sample collected from the mouth of a subject as it is as a liquid sample for fluorescence measurement. A genotype of interest can be thus determined easily.

Especially when a bacterial body is used in preparing a liquid sample, if a pH value of the liquid sample is adjusted to higher than pH 7.5 and not higher than pH 8.5 and is subjected to enzyme reaction before fluorescence measurement, a fluorescence intensity of type II or type IV becomes strong, which allows an improved accuracy in determining a genotype between type II or type IV and the other type. When a bacterial body-based extractive matter is used in preparing a liquid sample, if a pH value of the liquid sample is adjusted to not lower than pH 7.5 and not higher than pH 8.0 and is subjected to enzyme reaction before fluorescence measurement, a fluorescence intensity of type IV or type I becomes strong, which allows an improved accuracy in determining a genotype between type VI or type I and the other type or types. A pH value of a test agent for determining a genotype of microorganism responsible for periodontal disease can be previously adjusted to the pH as described above. A large number of adults with healthy periodontal tissue have Pg bacteria of type I, while a large number of adult patients with periodontitis have Pg bacteria of type II or type IV. The test agent described above can thus determine a current pathological condition or a possibility of aggravation of the periodontal disease more accurately.

A liquid sample can be prepared by using either a bacterial body contained in dental plaque, gingival fluid, or the like, or a bacterial body extracted from the bacterial body-based extractive matter. It has been known that behavior of enzyme activity in response to temperature conditions varies for each genotype and, at the same time, for each geometry of a specimen. Ability of a vesicle including an enzyme or the like to free from a bacterial body or ability of a bacterial body to retain a vesicle probably vans depending on genotypes. Adjustment of conditions of enzyme reaction for each geometry of a specimen allows, however, determination with high accuracy to be made.

<Florescence Measurement Device>

A fluorescence measurement device is described next with reference to the related drawings.

Figure 10:
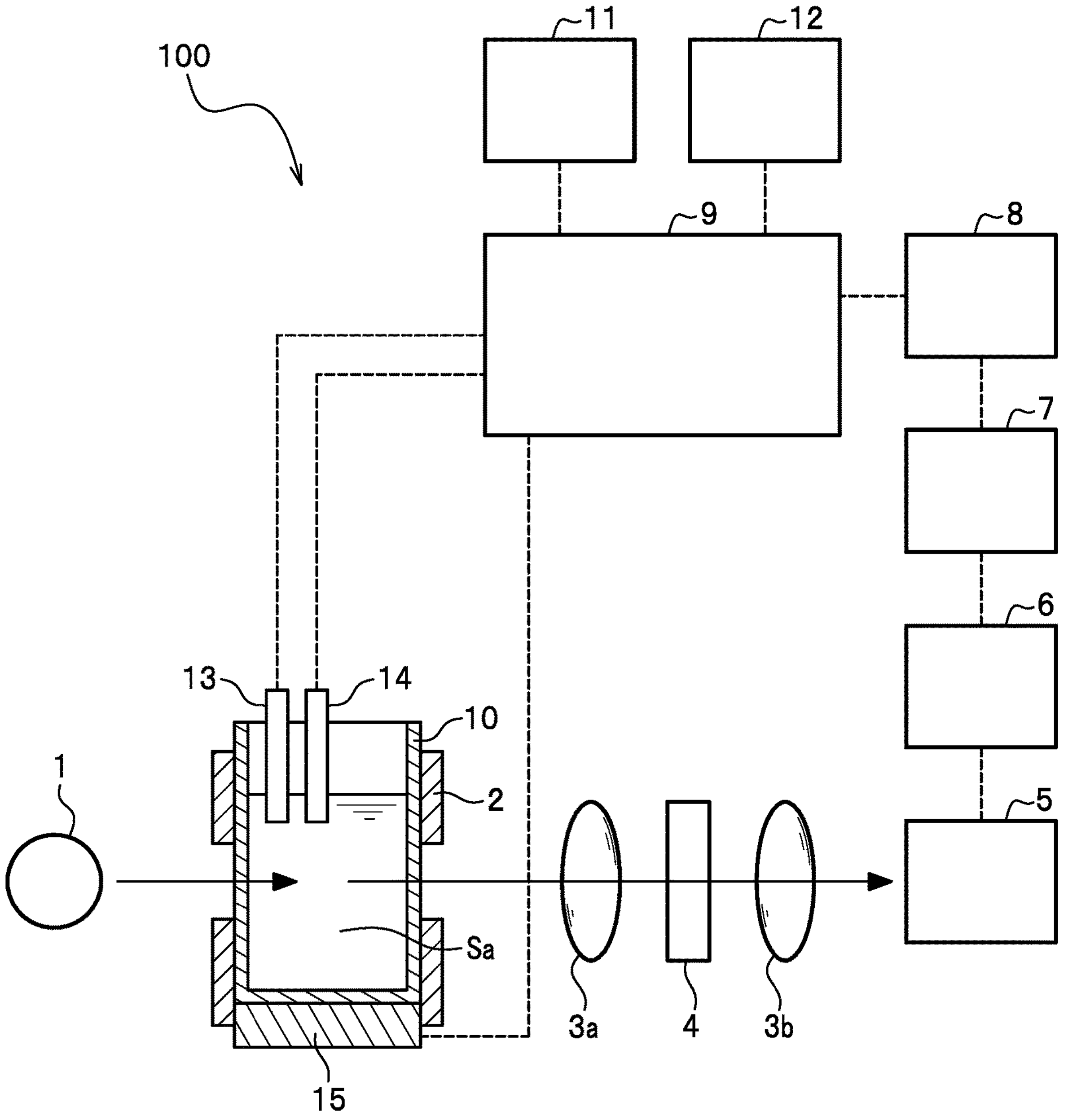
FIG. 10 is a diagram illustrating a structure of a fluorescence measurement device according to the embodiment of the present invention.

FIG. 10 is a diagram illustrating a structure of a fluorescence measurement device according to the embodiment of the present invention.

As illustrated in FIG. 10, a fluorescence measurement device 100 according to the embodiment includes: a light source (an irradiator) 1, a sample holder 2, optical lenses 3*a*, 3*b*, a filter 4, a detection element (a detector) 5, an amplifier 6, an analog processor 7, an ND converter 8, a controller (a determinator) 9, a sample container 10, an input means 11, a display means 12, a pH measurement means 13, a temperature measurement means 14, and a temperature control device 15.

The fluorescence measurement device 100 according to the embodiment is a fluorescence measurement device that can determine a genotype of a microorganism responsible for periodontal disease. The fluorescence measurement device 100 determines to which genotype of known polymorphic types a microorganism responsible for periodontal disease or a bacterial body-based extractive matter thereof (a specimen) contained in a liquid sample Sa belongs. The determination of a genotype is made based on an enzyme activity which has been confirmed to have a correlation with each of the genotypes. The enzyme activity is evaluated by a fluorometric method using a test agent with a fluorescently-labeled enzyme reaction substrate.

A microorganism responsible for periodontal disease (a bacteria specimen) targeted herein for determination of a genotype includes *Porphyromonas gingivalis* (Pg), as is the case with the above-described determination method according to the embodiment. Some examples of the genotypes to be determined include type I (type 1), type II (type 2), type III (type 3), type IV (type 4), and type V (type 5), which are polymorphic types of the fimA gene.

The bacteria specimen used herein includes, as is the case with the above-described determination method according to the embodiment: dental plaque, gingival fluid, or the like, collected from the mouth of a subject as it is; a suspension liquid thereof; and a supernatant of the suspension liquid. The liquid sample targeted for fluorescence measurement used herein includes the liquid sample Sa containing: a microorganism responsible for periodontal disease or a bacterial body-based extractive matter thereof; and a fluorescently-labeled substrate in which a substrate for enzyme reaction by the microorganism responsible for periodontal disease is fluorescently labeled (a reagent).

The light source 1 is a device for generating excitation light. When an enzyme reaction by the microorganism responsible for periodontal disease occurs in the liquid sample Sa, a fluorescent chromophore dissociates from the fluorescently-labeled substrate. When the liquid sample Sa is irradiated with the excitation light generated by the light source 1, the liquid sample Sa radiates fluorescence emitted from the fluorescent chromophore.

The light source 1 used herein preferably but not necessarily includes a monochromatic light source whose prescribed excitation wavelength is monochromatized, such as, for example, a light emitting diode (a LED) and a laser light source. The light source 1 may also include, however, another light source such as a xenon lamp, a mercury lamp, and a halogen lamp, together with an optical system such as a spectroscope.

The excitation light generated by the light source 1 preferably but not necessarily has a maximum peak at a wavelength not less than 350 nm and not more than 380 nm; more preferably, not less than 355 nm and not more than 375 nm; and, further preferably, not less than 360 nm and not more than 370 nm. When the fluorescent chromophore composing the fluorescently-labeled substrate is AMC, the excitation light with the above-described spectrum makes it possible to obtain a fluorescence intensity suitable for detection.

The sample holder 2: is disposed in a measurement room not illustrated; and supports the sample container 10 in a state of being capable of irradiating with excitation light and emitting fluorescence. When fluorescence is measured, the sample container 10 in which the liquid sample Sa has been put is fixed into the sample holder 2. The sample container 10 supported by the sample holder 2 is irradiated from a side thereof with the excitation light.

The detection element 5 is a device for detecting fluorescence emitted by the liquid sample Sa. The fluorescence emitted by the liquid sample Sa radiates from the sample container 10 and passes through the optical lens 3*a* to reach the filter 4. The filter 4 filters out noise or a low-sensitive wavelength band; and thus makes fluorescence in a specific wavelength band pass through. The fluorescence having passed through the filter 4: further passes through the optical lens 3*b*; enters the detection element 5; and is converted into an electrical signal.

The detection element 5 used herein includes various detection elements such as a photodiode, a phototube, and a photomultiplier tube. The filter 4 used herein includes an optical filter and a dichroic mirror. The filter 4 preferably but not necessarily: makes light at a wavelength not less than 410 nm and not more than 475 nm pass through; and blocks light at a wavelength other than the described above. The filter 4 having the above-described property makes it possible to obtain fluorescence with a high sensitivity, when the fluorescent chromophore composing the fluorescently-labeled substrate is AMC.

The electrical signal converted from the fluorescence by the detection element 5: is amplified by the amplifier 6; and is subjected to a denoising processing or the like by the analog processor 7 equipped with a low-pass filter or the like. The electrical signal of the fluorescence: is then converted into a digital signal by the ND converter 8; and is inputted into the controller 9.

A pH value of the liquid sample Sa whose fluorescence is to be measured is preferably but not necessarily is adjusted to higher than pH 7.5 and not higher than pH 8.5 and is then subjected to enzyme reaction, before the fluorescence measurement. The pH value of the liquid sample Sa is preferably not lower than pH 7.8. The pH value of the liquid sample Sa is also preferably not higher than pH 8.4; more preferably, not higher than pH 8.3; further preferably, not higher than pH 8.2; and, still further preferably, not higher than pH 8.1. When the pH value is controlled as described above, a genotype of the fimA gene of Pg bacteria can be determined more accurately.

The pH of the liquid sample Sa can be measured by the pH measurement means 13. The pH measurement means 13 used herein includes, for example, a pH meter of glass electrode type, membrane electrode type, or the like, which is used by being inserted into the sample container 10. The pH measurement means 13 can measure a pH of the liquid sample Sa at a time of the fluorescence measurement. This makes it possible to, when the pH is out of a prescribed range, take such an appropriate measure as stopping the fluorescence measurement or skipping an inaccurate result of the fluorescence measurement.

The liquid sample Sa whose fluorescence is to be measured is preferably but not necessarily subject to a fluorescence measurement at a constant temperature controlled at a prescribed temperature. The temperature of the liquid sample Sa is preferably but not necessarily, not lower than 4° C. and not higher than 45° C. When a bacterial body-based extractive matter is used, the temperature of the liquid sample Sa is preferably but not necessarily, not lower than 25° C.; more preferably, not lower than 30° C.; further preferably, not lower than 34° C.; and, still further preferably not lower than 36° C. Also in that case, the temperature of the liquid sample is preferably but not necessarily, not higher than 40° C.; more preferably, not higher than 39° C.; and, further preferably, not higher than 38° C. Meanwhile, when a bacterial body is used, a temperature of the liquid sample Sa is preferably but not necessarily, not lower than 4° C.; more preferably, not lower than 10° C.; further preferably, not lower than 15° C.; still further preferably not lower than 18° C.; and, yet further preferably not lower than 21° C. Also in that case, the temperature of the liquid sample Sa is preferably but not necessarily, not higher than 37° C.; more preferably, not higher than 30° C.; further preferably, not higher than 26° C.; and, yet further preferably, not higher than 23° C. When the temperature is adjusted as described above, a genotype of the fimA gene of Pg bacteria can be determined more accurately.

A temperature of the liquid sample Sa can be measured by the temperature measurement means 14. The temperature measurement means 14 used herein is, for example, a thermistor, a thermocouple, a resistance thermometer, or the like, which is used by being inserted into the sample container 10. The temperature measurement means 14 can: monitor a temperature of the liquid sample Sa at a time of fluorescence measurement online; and provide feedback control over the temperature control device 15.

The temperature control device 15 is a device for controlling a temperature of the liquid sample Sa in the sample container 10. The temperature control device 15 used herein is a PTC (Positive Temperature Coefficient) heater, a Peltier device, a constant-temperature medium circulation system, or the like, which can be installed around the sample container 10, for example, at the sample holder 2 disposed below or on a lateral side of the sample container 10. The temperature control device 15 described above can control a temperature of the liquid sample Sa at a temperature suitable for enzyme reaction. This makes it possible to accurately evaluate the enzyme activity.

Note that the fluorescence measurement device 100 illustrated in FIG. 10 uses the sample container 10 in form of a cell. The sample container 10 used herein may be, however, a microtube. Such a microtube can be used in various operations such as reaction, extraction, culture, and centrifugal separation; and may be a container made of plastic, glass, or the like, with a volume of about 1 ml to about 2 ml.

When a microtube is used as the sample container 10, the microtube without a lid thereon, in which the liquid sample Sa has been put can be placed into the sample holder 2*a*. The microtube as described above allows excitation light to enter therein from a lateral wall surface thereof. Fluorescence emitted from the liquid sample Sa can be detected by making the fluorescence emitted not from a lateral side of the sample holder 2 but from a top of the microtube without a lid thereon.

When the microtube is configured as described above, a lateral wall of the microtube serves as an optical waveguide of the excitation light and fluorescence is emitted from above the microtube without the lid, which can make an optical system simple. Additionally, such a microtube can be used in various operations and is then subjected to fluorescence measurement as it is. This makes it possible to: prepare only a small amount of the liquid sample Sa as a target to be measure; use a fluorescence measurement device having a simple structure; and thereby measure fluorescence in the liquid sample Sa easily and inexpensively.

Figure 11:
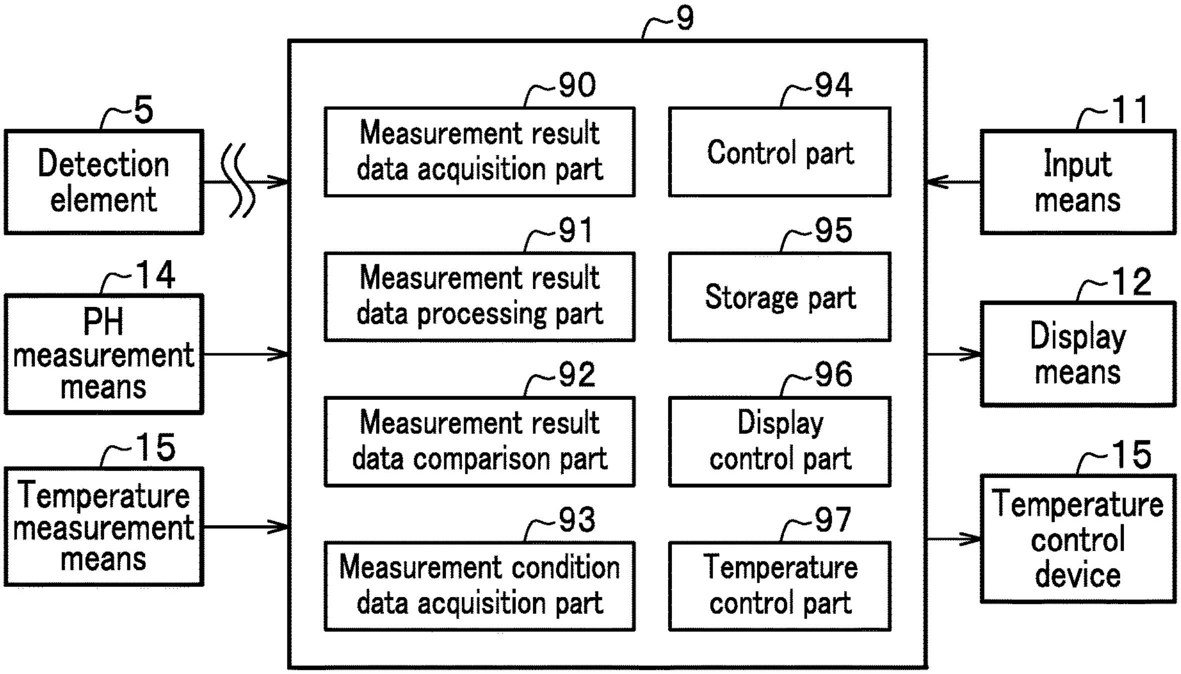
FIG. 11 is a diagram illustrating an outline of a structure of a controller included in the fluorescence measurement device.

FIG. 11 is a diagram illustrating an outline of a structure of the controller 9 included in the fluorescence measurement device 100.

As illustrated in FIG. 11, the controller 9 of the fluorescence measurement device 100 includes a measurement result data acquisition part 90, a measurement result data processing part 91, a measurement result data comparison part 92, a measurement condition data acquisition part 93, a control part 94, a storage part 95, a display control part 96, and a temperature control part 97.

The controller 9: controls operations of the fluorescence measurement device 100; and determines a genotype of a microorganism responsible for periodontal disease or a bacterial body-based extractive matter thereof contained in the liquid sample Sa. The controller 9 is configured by a processor such as a CPU (Central Processing Unit) or a memory such as a ROM (Read Only Memory), a RAM (Random Access Memory), and a hard disk.

The controller 9 is connected to each of the input means 11, the detection element 5 included in a fluorescence measurement part, the pH measurement means 14, and the temperature measurement means 15, via an input interface not illustrated. The controller 9 is connected to each of the display means 12 and the temperature control device 15 via an output interface not illustrated. Those devices included in the controller 9 are connected to each other via a bus not illustrated.

The input means 11 is a device for operating the fluorescence measurement device 100. The input means 11 is realized by any of various devices, for example, a keyboard, a mouse, and a touchpad.

The display means 12 is a device for displaying a result of determination of a genotype. The display means 12 is realized by any of various devices, for example, a liquid crystal display, a plasma display, and an organic electroluminescent display.

The fluorescence measurement device 100 can determine a genotype of a microorganism responsible for periodontal disease or a bacterial body-based extractive matter thereof contained in the liquid sample Sa, by using a method of comparing: a value of fluorescence intensity or an amount of change over time of fluorescence intensity of a liquid sample containing the microorganism responsible for periodontal disease or a bacterial body-based extractive matter thereof, whose genotype is not yet known; and a preset threshold. The comparison is made: between the value of fluorescence intensity and a threshold corresponding thereto; or between the amount of change over time of fluorescence intensity and a threshold corresponding thereto.

The measurement result data acquisition part 90 acquires data on a result of measurement inputted from the fluorescence measurement part including the detection element 5. The measurement result data includes data on a fluorescence intensity of fluorescence detected from the liquid sample Sa and a measurement time starting at a beginning of an enzyme reaction of interest. The measurement result data is outputted to the measurement result data processing part 91 or the storage part 95.

The measurement result data processing part 91 calculates data on fluorescence intensity used for determining a genotype, based on the measurement result data. The data on fluorescence intensity includes data on a value of fluorescence intensity at a prescribed detection time and an amount of change over time of fluorescence intensity (a slope) at a prescribed detect time. The data on fluorescence intensity may be an average value of values of fluorescence intensity in a prescribed time period of detection times, an average value of amounts of change over time of fluorescence intensity (a slope) in a prescribed time period of detection times, or or a maximum value thereof. The data on fluorescence intensity is outputted to the measurement result data comparison part 92 or the storage part 95.

The measurement result data comparison part 92 compares a data on fluorescence intensity with a threshold stored in the storage part 95. The measurement result data comparison part 92: determines whether or not the generated data on fluorescence intensity of the liquid sample Sa exceeds the threshold; and determines a genotype of the microorganism responsible for periodontal disease or a bacterial body-based extractive matter thereof contained in the liquid sample Sa. Data on a result of the determination is outputted to the display control part 97.

The measurement condition data acquisition part 93 acquires a data on measurement condition inputted from the pH measurement means 13 or the temperature measurement means 14. The measurement condition data is a data on a pH of the liquid sample Sa measured by the pH measurement means 13 in a prescribed time intervals or a data on a temperature of the liquid sample Sa measured by the temperature measurement means 14 in a prescribed time intervals. The measurement condition data is outputted to the control part 95 or the temperature control part 97.

The control part 94 provides control over: operations of the devices included in the fluorescence measurement device 100; a processing of determining a genotype of a microorganism responsible for periodontal disease; a processing of displaying a result of the determination; or the like, based on a prescribed program or an input from a user via the input means 11.

The storage part 95 stores therein a program of executing: operations of the devices included in the fluorescence measurement device 100; a processing of determining a genotype of a microorganism responsible for periodontal disease; a processing of displaying a result of the determination; or the like, or data on a threshold used in determining a genotype, or the like.

The following processing is possible, for example. Fluorescence of a microorganism responsible for periodontal disease or a bacterial body-based extractive matter thereof, whose genotype is already known, is measured in advance. A fluorescence intensity data is calculated from a measurement result data obtained as a result of the measurement. The calculated fluorescence intensity data can be thus stored in the storage part 95 previously. Additionally, a threshold for each genotype is set in advance, based on a number of fluorescence intensity data, and the set threshold can be thus stored in the storage part 95 previously.

In setting a threshold as described above, various analysis techniques can be used such as, for example, regression analysis, standard deviation classification, natural breaks, and multiclass classification. The set threshold can be previously corrected so as not to be affected by enzyme activity other than a degrading enzyme targeted for evaluation.

The display control part 96 provides control over generation or display of an image to be displayed in the display means 12. The display control part 96: generates an image showing an operation state of the fluorescence measurement device 100, a result of fluorescence measurement or of determination of a genotype, or the like; and outputs the generated image to the display means 12.

The temperature control part 97 provides control over a temperature of the temperature control device 15. The temperature control part 97: feedback controls the temperature control device 15 based on a temperature of the liquid sample Sa measured by the temperature measurement means 14; and keeps the temperature of the liquid sample Sa at a temperature suitable for enzyme reaction.

Figure 12:
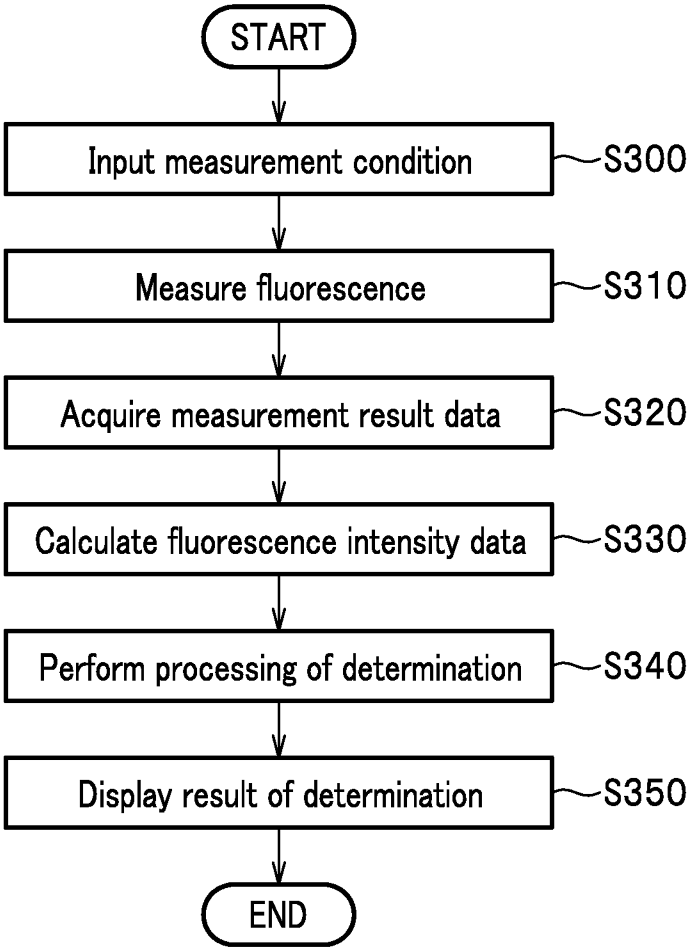
FIG. 12 is a flowchart illustrating steps of a determination method performed by the fluorescence measurement device.

FIG. 12 is a flowchart illustrating steps of a determination method performed by the fluorescence measurement device.

As illustrated in FIG. 12, the fluorescence measurement device 100: measures fluorescence of the liquid sample Sa targeted for the measurement and containing a microorganism responsible for periodontal disease or a bacterial body-based extractive matter thereof (a specimen), whose genotype is not yet known; and displays a resultant genotype determined based on the measurement data displayed to a user.

As illustrated in FIG. 12, an operation of the fluorescence measurement device 100 starts with an input of a measurement condition of a fluorescence measurement to the controller 9 (step S300). The measurement condition used herein includes: a type of a specimen used in preparing a liquid sample; a fluorescence wavelength used for the fluorescence measurement; a waiting/detection time; a type of data on fluorescence intensity used for determination of a genotype such as, for example, a value of fluorescence intensity at a prescribed detection time and an amount of change over time of fluorescence intensity (a slope) at a prescribed detection time.

The fluorescence measurement of the liquid sample Sa containing the microorganism responsible for periodontal disease or the bacterial body-based extractive matter (the specimen), whose genotype is not yet known, is started. The liquid sample Sa is irradiated with excitation light and is subjected to fluorescence detection (step S310). A measurement result data is acquired therefrom, which is an electrical signal of the fluorescence detected by the detection element 5 (step S320).

In step S320, when a value of fluorescence intensity at a prescribed detect time is used for determining a genotype, then the value of fluorescence intensity at the prescribed time is collected in the measurement result data acquisition part 90, as the measurement result data. When an amount of change over time of fluorescence intensity (a slope) is used for determining a genotype, values of fluorescence intensity at prescribed intervals are collected with time in the measurement result data acquisition part 90, as the measurement result data. When an average value or a maximum value is used, values of fluorescence intensity in a prescribed time period are collected.

A fluorescence intensity data used for determining a genotype is calculated based on the measurement result data (step S330). The fluorescence intensity data is collected in the measurement result data processing part 91, as a value of fluorescence intensity at a prescribed detection time, the average value of values of fluorescence intensity in a prescribed detection time period, the amount of change over time of fluorescence intensity (the slope) at a prescribed detection time, or the average value or the maximum value of amounts of change over time of fluorescence intensity (the slope) in a prescribed detection time period.

A processing is performed in which a genotype of the microorganism responsible for periodontal disease or the bacterial body-based extractive matter (the specimen), whose genotype is not yet known, is determined (step S340). The display control part 96 makes the display means 12 display an image showing a result of determining the genotype (step S350). The fluorescence measurement device 100 then terminates the operation thereof.

What is displayed in the display means 12 as the result of determination of the genotype includes: whether or not the microorganism responsible for periodontal disease or the bacterial body-based extractive matter thereof contained in the liquid sample Sa, whose genotype is not yet known, belongs to any of known genotypes; and that the genotype is indeterminable. The determination result may be displayed in any of a language, a symbol, a color or the like, or may be displayed with a percentage or the like representing an accuracy of the determination.

Figure 13:
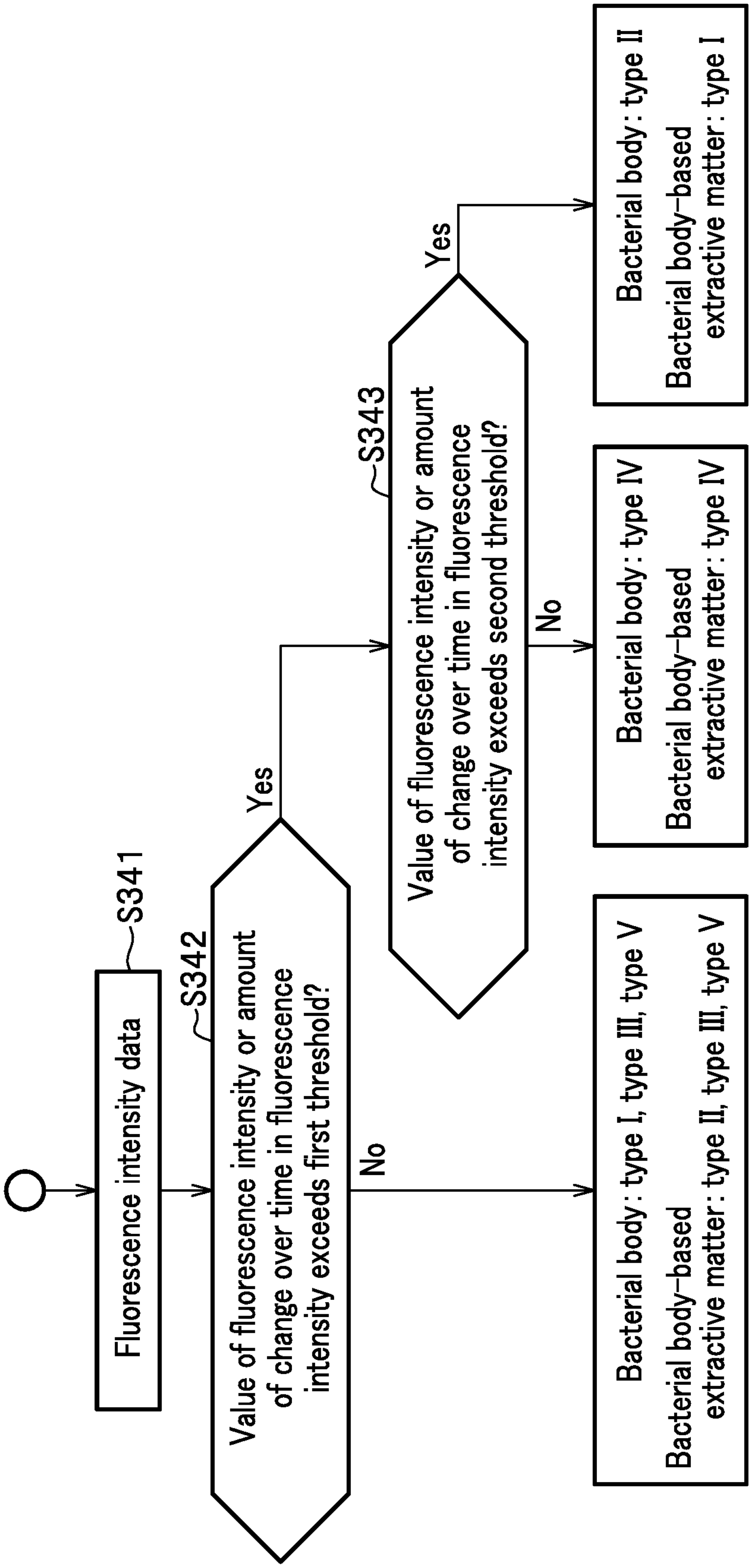
FIG. 13 is a flowchart illustrating steps of a processing of determining a genotype performed by the fluorescence measurement device.

FIG. 13 is a diagram illustrating steps of determining a genotype performed by the fluorescence measurement device.

As illustrated in FIG. 13, the measurement result data comparison part 92 performs the step of determining a genotype of a microorganism responsible for periodontal disease or a bacterial body-based extractive matter thereof, whose genotype is not yet known (step S340), by comparing the fluorescence intensity data which is a data on a value of fluorescence intensity or an amount of change over time of fluorescence intensity, with a threshold stored in the storage part 95.

The measurement result data comparison part 92 allows therein an input of a fluorescence intensity data on a liquid sample containing a microorganism responsible for periodontal disease or a bacterial body-based extractive matter (a specimen), whose genotype is not yet known (step S341).

The fluorescence intensity data, that is, a value of fluorescence intensity or an amount of change over time of fluorescence intensity, of the liquid sample containing the microorganism responsible for periodontal disease or the bacterial body-based extractive matter (the specimen), whose genotype is not yet known, is compared with a predetermined first threshold (step S342).

As a result of the comparison with the first threshold, if the fluorescence intensity data of the liquid sample, that is, the value of fluorescence intensity or the amount of change over time of fluorescence intensity, whose genotype is not yet known, exceeds the first threshold (step S342: Yes), then the processing advances to step S343.

The fluorescence intensity data, that is, the value of fluorescence intensity or the amount of change over time of fluorescence intensity, of the liquid sample containing the microorganism responsible for periodontal disease (a bacteria specimen), whose genotype is not yet known, is compared with a predetermined second threshold (step S343).

Any appropriate value can be set as each of the first threshold and the second threshold, by: previously measuring fluorescence of a microorganism responsible for periodontal disease or a bacterial body-based extractive matter thereof, whose genotype is already known; and setting an appropriate value based on a correlation between a resultant fluorescence intensity and a reaction time, depending on a genotype as a target for determination or a condition of enzyme reaction. A value which can be set herein includes, for example, a boundary value which distinguishes between type I and type IV and that between type IV and type II, which makes a distinction between the shaded areas in FIG. 8 and FIG. 9, respectively.

When a bacterial body is used in preparing a liquid sample, the first threshold can be set based on, for example, either or both of: a value of fluorescence intensity or an amount of change over time of fluorescence intensity of a liquid sample containing a bacterial body of the microorganism responsible for periodontal disease, whose genotype of the fimA gene is type I; and a value of fluorescence intensity or an amount of change over time of fluorescence intensity of a liquid sample containing the bacterial body of the microorganism responsible for periodontal disease, whose genotype of the fimA gene is type IV. More specifically, the first threshold can be set, for example, as follows. A number of results of fluorescence measurement of liquid samples are previously obtained, which have substantially the same conditions as that of the liquid sample Sa targeted for determination of a genotype, such as a pH, a temperature, a specimen amount of the microorganism responsible for periodontal disease, and a concentration of a fluorescently-labeled substrate. From among the results, such a boundary value is obtained that has a value not larger than a maximal value of the collected fluorescence measurement results with respect to type I, and at the same time, has a value smaller than a minimal value thereof with respect to type IV. The boundary value can be thus set as the first threshold, based on the results of change over time in fluorescence intensity. In this case in which a bacterial body is used in preparing a liquid sample, the first threshold makes it possible to distinguish between type I and type IV or type II.

When a bacterial body-based extractive matter is used in preparing a liquid sample, the first threshold can be set based on, for example, either or both of: a value of fluorescence intensity or an amount of change over time of fluorescence intensity of a liquid sample containing a bacterial body-based extractive matter of the microorganism responsible for periodontal disease, whose genotype of the fimA gene is type II; and a value of fluorescence intensity or an amount of change over time of fluorescence intensity of a liquid sample containing a bacterial body-based extractive matter of the microorganism responsible for periodontal disease, whose genotype of the fimA gene is type IV. In this case in which the bacterial body-based extractive matter is used in preparing a liquid sample, the first threshold makes it possible to distinguish between type II and type IV or type I.

When a bacterial body is used in preparing a liquid sample, the second threshold can be set based on, for example, either or both of: a value of fluorescence intensity or an amount of change over time of fluorescence intensity of a liquid sample containing a bacterial body of the microorganism responsible for periodontal disease, whose genotype of the fimA gene is type IV; and a value of fluorescence intensity or an amount of change over time of fluorescence intensity of a liquid sample containing a bacterial body of the microorganism responsible for periodontal disease, whose genotype of the fimA gene is type II. More specifically, the second threshold can be set, for example, as follows. A number of results of fluorescence measurement of liquid samples are previously obtained, which have substantially the same conditions as that of the liquid sample Sa targeted for determination of a genotype, such as a pH, a temperature, a specimen amount of the microorganism responsible for periodontal disease, and a concentration of a fluorescently-labeled substrate. From among the results, such a boundary value is obtained that has a value not larger than a maximal value of the collected fluorescence measurement results with respect to type IV, and at the same time, has a value smaller than a minimal value thereof with respect to type II, The boundary value can be thus set as the second threshold, based on the results of change over time in fluorescence intensity. In this case in which the bacterial body is used in preparing a liquid sample, the second threshold makes it possible to distinguish between type II and type IV or type I.

When a bacterial body-based extractive matter is used in preparing a liquid sample, the second threshold can be set based on, for example, either or both of: a value of fluorescence intensity or an amount of change over time of fluorescence intensity of a liquid sample containing a bacterial body-based extractive matter of the microorganism responsible for periodontal disease, whose genotype of the fimA gene is type IV; and a value of fluorescence intensity or an amount of change over time of fluorescence intensity of a liquid sample containing a bacterial body-based extractive matter of the microorganism responsible for periodontal disease, whose genotype of the fimA gene is type I. In this case in which the bacterial body-based extractive matter is used in preparing a liquid sample, the second threshold makes it possible to distinguish between type I and type IV or type II.

When a bacterial body is used in preparing a liquid sample, as a result of comparison with the thresholds, if the resultant fluorescence intensity data, that is, the value of fluorescence intensity or the amount of change over time of fluorescence intensity of the liquid sample, whose genotype is not yet known, is larger than the first threshold and not larger than the second threshold (step S342: Yes, step S343: No), then the fimA gene of the microorganism responsible for periodontal disease of the liquid sample is determined to be of a genotype other than type I or type II. That is, when the bacteria specimen does not contain a genotype other than type III or type V, the genotype of interest is determined to be of type IV. When a bacterial body-based extractive matter of the bacterial body is used in preparing a liquid sample, the fimA gene of the microorganism responsible for periodontal disease in the liquid sample is determined to be of a genotype other than type II or type I. That is, when the bacteria specimen does not contain the genotype other than type III or type V, the genotype of interest is determined to be type IV.

When a bacterial body is used in preparing a liquid sample, as a result of comparison with the threshold, if the resultant fluorescence intensity data, that is, the value of fluorescence intensity or the amount of change over time of fluorescence intensity of a liquid sample, whose genotype is not yet known, is larger than the second threshold (step S342: Yes and step S343: No), then the fimA gene of the microorganism responsible for periodontal disease of the liquid sample is determined to be of a genotype other than type I or type IV. That is, when the bacteria specimen does not contain a genotype other than type III or type V, the genotype of interest is determined to be of type II. When a bacterial body-based extractive matter of the bacterial body is used in preparing a liquid sample, the fimA gene of the microorganism responsible for periodontal disease in the liquid sample is determined to be of a genotype other than type II or type IV. That is, when the bacteria specimen does not contain a genotype other than type III or type V, the genotype of interest is determined to be type I.

When a still another bacterial body is used in preparing a liquid sample, as a result of comparison with the thresholds, if the resultant fluorescence intensity data, that is, the value of fluorescence intensity or the amount of change over time of fluorescence intensity of a liquid sample, whose genotype is not yet known, is not larger than the first threshold (step S342: No), then the fimA gene of the microorganism responsible for periodontal disease of the liquid sample is determined to be of a genotype other than type II or type IV. That is, when the bacteria specimen does not contain a genotype other than type III or type V, the genotype of interest is determined to be type I. When a bacterial body-based extractive matter is used in preparing a liquid sample, the fimA gene of the microorganism responsible for periodontal disease in the liquid sample is determined to be of a genotype other than type IV or type I. That is, when the bacteria specimen does not contain a genotype other than type III or type V, the genotype of interest is determined to be type II.

When enzyme activity of a microorganism responsible for periodontal disease has correlation with a genotype thereof, the determination method according to the present embodiment described above can determine the genotype of the microorganism responsible for periodontal disease, based on the enzyme activity obtained by the fluorometric method. Unlike the conventionally-used molecular biology techniques, the determination method according to the embodiment can make the determination taking into account an enzyme activity which advances the periodontal disease. This allows the determination of a genotype to be met with an actual pathological condition. Additionally, the determination method according to the embodiment makes it possible to use a specimen collected from the mouth of a subject as it is as a liquid sample for fluorescence measurement. A genotype of interest can be thus determined easily.

The fluorescence measurement device can include, in particular, a storage part in which the first threshold or the second threshold is stored. This makes it possible to determine a genotype of a microorganism responsible for periodontal disease with excellent stability and reproducibility, irrespective of performed manipulation or operation. An automatic determination of a genotype of the microorganism responsible for periodontal disease can be made by just preparing a sample collected from the mouth of a subject having the responsible microorganism and a test agent for the determination of a genotype of the responsible microorganism. Consequently, a current pathological condition or a possible aggravation of the periodontal disease of the subject can be determined efficiently.

The present invention described above is not limited to that having all of the configurations explained in the above-described embodiment, and various changes are possible within a scope not departing from the gist of the present invention. For example, part of a configuration according to the embodiment may be substituted by or added to another configuration. Alternatively, part of a configuration according to the embodiment may be deleted.

The above-described fluorescence measurement device 100 can include, for example, an appropriate optical or signal processing system, as long as the device 100 can measure a fluorescence intensity of the liquid sample Sa. A genotype may be determined by using not only the first threshold or the second threshold but also any other techniques of comparing similarities between index values of fluorescence intensities such as a technique similar to the above-described determination method.

DESCRIPTION OF REFERENCE NUMERALS

1 light source (irradiator)
2 sample holder
3*a* optical lens
3*b* optical lens
4 filter
5 detection element (detector)
6 amplifier
7 analog processor
8 ND converter
9 controller (determinator)
10 sample container
11 input means
12 display means
13 pH measurement means
14 temperature measurement means
15 temperature control device
90 measurement result data acquisition part
91 measurement result data processing part
92 measurement result data comparison part
93 measurement condition data acquisition part
94 control part
95 storage part
96 display control part
97 temperature control part
100 fluorescence measurement device

The invention claimed is:

1. A liquid sample in combination with a test agent that determines genotypes I, II, and IV of Porphyromonas gingivalis, wherein the liquid sample includes:

an experimental liquid sample in a container, containing a bacterial body or a bacterial body-based extractive matter of *Porphyromonas gingivalis*, whose genotype is not yet known, wherein the experimental liquid sample is collected from a subject suffering from a periodontal-pathological condition;

the test agent comprising:

a reagent including a protective-group-glycyl-glycyl-L-arginyl-4-methylcoumaryl-7-amide as a substrate that is fluorescently labeled; and a pH buffer solution wherein a pH of the pH buffer solution is not lower than pH 7.0 and not higher than pH 8.5, wherein the test agent includes a series of sample containers, wherein the series of sample containers contains either a series of bacterial bodies of *Porphyromonas gingivalis*, or a series of bacterial body-based extractive matters of *Porphyromonas gingivalis*, whose genotypes are are polymorphic types I, II, and IV of a fimA gene, and further wherein, in determining the genotype for the experimental liquid sample, if a value of fluorescence intensity or an amount of change over time of fluorescence intensity of the experimental liquid sample is the same as or similar to a value of fluorescence intensity or an amount of change over time of fluorescence intensity of the test agent, when the test agent and the experimental liquid sample match in their contents of either bacterial bodies or bacterial body-based extractive matters, then a genotype of the fimA gene within the experimental liquid sample is determined to be the same as that in the test agent.

2. A determination method of determining genotypes I, II, and IV of *Porphyromonas gingivalis*, comprising the steps of:

providing a fluorescence measurement device comprising:

a light source that emits an excitation light, a detector positioned to receive the excitation light emitted by the light source after the excitation light exits a liquid sample container, and a determinator that receives modified data from the detector;

providing a series of liquid samples that include a reagent, wherein the reagent contains a fluorescently labeled substrate of a protective-group-glycyl-glycyl-L-arginyl-4-methylcoumaryl-7-amide, and further wherein the series of liquid samples have a pH value not lower than pH 7.0 and not higher than pH 8.5, whereby providing the series of liquid samples starts an enzymatic reaction;

providing and irradiating a series of controls in the series of liquid samples with the light source, wherein each control of the series of controls contains a different bacterial body of a single strain of *Porphyromonas gingivalis* having a known genotype of a fimA gene, wherein a series of control thresholds of fluorescence measurements comprises three bacterial body thresholds, wherein a first bacterial body threshold is derived from the control containing genotype I of the fimA gene, a second bacterial body threshold is derived from the control containing genotype IV of the fimA gene, and a third bacterial body threshold is derived from the control containing genotype II of the fimA gene;

collecting the fluorescence measurements emitted from each of the irradiated controls with the fluorescence measurement device, wherein each bacterial body threshold is the measured value of fluorescence intensity, or an amount of change over time of fluorescence intensity of the irradiated controls;

obtaining an experimental sample from a subject having a current periodontal-pathological condition and placing the experimental sample into an experimental liquid sample within the series of liquid samples;

irradiating the experimental liquid sample with the light source, wherein the experimental liquid sample includes a bacterial body of a microorganism responsible for periodontal disease, collecting a fluorescence measurement emitted from the experimental liquid sample with the fluorescence measurement device, wherein the collection of emitted fluorescence is measured as a change in fluorescence intensity between zero and ten minutes of the start of the enzymatic reaction; and determining a genotype of the fimA gene of the experimental sample, wherein the determinator compares the fluorescence measurement from the experimental sample to the series of thresholds and determines the genotype of the fimA gene of the experimental sample by determining the similarity of the fluorescence emitted from the experimental liquid sample to one of the three bacterial body control thresholds of the series of control thresholds, wherein the bacterial body experimental liquid sample is determined to contain the fimA genotype I, IV, or II, with respect to the fluorescence intensity in that order, where type I has the largest intensity.

3. The determination method according to claim 2, wherein the reagent is isobutyloxycarbonyl-glycyl-glycyl-L-arginyl-4-methylcoumaryl-7-amide (iBoc-Gly-Gly-Arg-MCA).

4. The determination method according to claim 2, wherein the excitation light is not less than 355 nm and not more than 375 nm.

5. The determination method according to claim 2, wherein the emitted fluorescence is not less than 430 nm and not more than 455 nm.

6. The determination method according to claim 2, wherein the liquid sample further comprises a pH buffer solution containing trihydroxymethylaminomethane (Tris).

7. The determination method according to claim 2, wherein a temperature of the liquid sample is not lower than 4° C. and not higher than 45° C.

8. A determination method of determining genotypes I, II, and IV of *Porphyromonas gingivalis*, comprising the steps of:

providing a fluorescence measurement device comprising:

a light source that emits an excitation light, a detector positioned to receive the excitation light emitted by the light source after the excitation light exits a liquid sample container, and a determinator that receives modified data from the detector;

providing a series of liquid samples that include a reagent, wherein the reagent contains a fluorescently labeled substrate of a protective-group-glycyl-glycyl-L-arginyl-4-methylcoumaryl-7-amide, and further wherein the series of liquid samples have a pH value not lower than pH 7.0 and not higher than pH 8.5, whereby providing the series of liquid samples starts an enzymatic reaction;

providing and irradiating a series of controls in the series of liquid samples with the light source, wherein a single control of the series of controls contains a different extractive matter of a single strain of *Porphyromonas gingivalis* having a known genotype of a fimA gene, wherein a series of control thresholds of fluorescence measurements comprises three extractive matter thresholds, wherein a first extractive matter threshold is derived from the control containing genotype II of the fimA gene, a second extractive matter threshold is derived from the control containing genotype IV of the fimA gene, and a third extractive matter threshold is derived from the control containing genotype I of the fimA gene;

collecting the fluorescence measurements emitted from each of the irradiated controls with the fluorescence measurement device, wherein each extractive matter threshold is the measured value of fluorescence intensity, or an amount of change over time of fluorescence intensity of the irradiated controls;

obtaining an experimental sample from a subject having a current periodontal-pathological condition and placing the experimental sample into an experimental liquid sample within the series of liquid samples;

irradiating the experimental liquid sample with the light source, wherein the experimental liquid sample includes an extractive matter of a microorganism responsible for periodontal disease, collecting a fluorescence measurement emitted from the experimental liquid sample with the fluorescence measurement device, wherein the collection of emitted fluorescence is measured as a change in fluorescence intensity between zero and ten minutes of the start of the enzymatic reaction; and determining a genotype of the fimA gene of the experimental sample, wherein the determinator compares the fluorescence measurement from the experimental sample to the series of thresholds and determines the genotype of the fimA gene of the experimental sample by determining the similarity of the fluorescence emitted from the experimental liquid sample to one of the three extractive matter control thresholds of the series of control thresholds, and further wherein the extractive matter experimental liquid sample is determined to contain the fimA genotype of type II, IV, or I, with respect to the fluorescence intensity in that order, where type II has the largest intensity.

9. The determination method according to claim 8, wherein the reagent is isobutyloxycarbonyl-glycyl-glycyl-L-arginyl-4-methylcoumaryl-7-amide (iBoc-Gly-Gly-Arg-MCA).

10. The determination method according to claim 8, wherein the excitation light is not less than 355 nm and not more than 375 nm.

11. The determination method according to claim 8, wherein the emitted fluorescence is not less than 430 nm and not more than 455 nm.

12. The determination method according to claim 8, wherein the liquid sample further comprises a pH buffer solution containing trihydroxymethylaminomethane (Tris).

13. The determination method according to claim 8, wherein a temperature of the liquid sample is not lower than 4° C. and not higher than 45° C.

* * * * *